United States Patent
Kuwabara et al.

(10) Patent No.: US 9,935,272 B2
(45) Date of Patent: Apr. 3, 2018

(54) LIGHT-EMITTING MATERIAL, ORGANIC LIGHT-EMITTING DEVICE, AND COMPOUND

(71) Applicant: KYULUX, INC., Fukuoka-shi, Fukuoka (JP)

(72) Inventors: Hirokazu Kuwabara, Tokyo (JP); Chihaya Adachi, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 0 days.

(21) Appl. No.: 15/112,268

(22) PCT Filed: Jan. 14, 2015

(86) PCT No.: PCT/JP2015/050722
§ 371 (c)(1),
(2) Date: Jul. 18, 2016

(87) PCT Pub. No.: WO2015/108049
PCT Pub. Date: Jul. 23, 2015

(65) Prior Publication Data
US 2016/0343953 A1 Nov. 24, 2016

(30) Foreign Application Priority Data
Jan. 17, 2014 (JP) .................. 2014-006609

(51) Int. Cl.
| C07D 413/14 | (2006.01) |
| C07D 401/14 | (2006.01) |
| C09K 11/06 | (2006.01) |
| H01L 51/00 | (2006.01) |
| H01L 51/50 | (2006.01) |

(52) U.S. Cl.
CPC ........ *H01L 51/0067* (2013.01); *C07D 401/14* (2013.01); *C07D 413/14* (2013.01); *C09K 11/06* (2013.01); *H01L 51/0071* (2013.01); *H01L 51/0072* (2013.01); *C09K 2211/1007* (2013.01); *C09K 2211/1074* (2013.01); *C09K 2211/1077* (2013.01); *H01L 51/5012* (2013.01)

(58) Field of Classification Search
CPC . C07D 401/14; C07D 413/14; H01L 51/0067; H01L 51/0071; H01L 51/0072; C09K 11/06
USPC .......................................................... 544/35
See application file for complete search history.

(56) References Cited

U.S. PATENT DOCUMENTS 8,911,886 B2 12/2014 Iwakuma et al.

FOREIGN PATENT DOCUMENTS

| CN | 103503188 | 1/2014 |
| JP | 2004331586 A | 11/2004 |
| JP | 4060802 B2 | 3/2008 |
| JP | 2009170815 A | 7/2009 |
| KR | 20110114229 A | 10/2011 |
| KR | 20130007390 A | 1/2013 |
| KR | 20130113357 A | 10/2013 |
| WO | 2011071255 A1 | 6/2011 |
| WO | 2012149999 A1 | 11/2012 |

OTHER PUBLICATIONS

International Search Opinion, dated Jan. 14, 2015 in corresponding application No. PCT/JP2015/050722.
Valchanov et al "Tuning the optical absorption of potential blue emitters" Organic Electronics, Aug. 2, 2013, 14 : (11) : 2727-2736 (2013).
Hanss et al "Variation of charge transfer kinetics in structurally closely related dyads with rhenium photosensitizers" Inorganica Chemica Acta, 362 :(10) 3415-3420 (Feb. 8, 2009).
Ciana et al "Synthesis of Side-Chain Derivatives of 2,2-Bipyridine" The Journal of Organic Chemistry, 54 (7):1731-1735 (Mar. 1, 1989).

(Continued)

*Primary Examiner* — Kahsay Habte
(74) *Attorney, Agent, or Firm* — Browdy and Neimark, PLLC

(57) ABSTRACT

A compound represented by the following general formula (1) is useful as a light-emitting material. $Y^1$ and $Y^2$ each independently represent N or $C(R^7)$; and $R^1$ to $R^7$ each independently represent a hydrogen atom or a substituent, provided that at least one of $R^1$ and $R^2$, and at least one of $R^5$ and $R^6$ represent a group represented by the following general formula (2). Z represent a divalent linking group having a linking chain length of 1 atom; $L^1$ represents a single bond or a substituted or unsubstituted arylene group; and $R^{11}$ to $R^{18}$ each independently represent a hydrogen atom or a substituent.

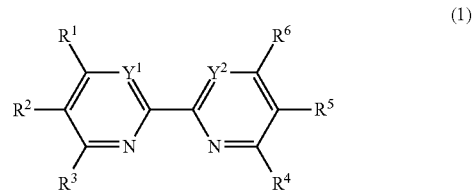

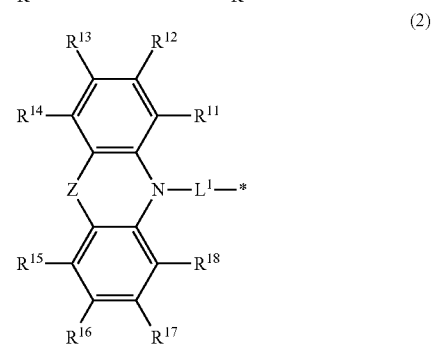

13 Claims, 5 Drawing Sheets

(56) References Cited

OTHER PUBLICATIONS

Suzuki et al "Ru (II) complexes with new redox-active 1.10-phenanthroline derivative: structural, spectral, and electrochemical investigations" Inorganica Chemica Acta, 357, 4335-4340 (2004).
International Search Report and Search Opinion dated, Mar. 10, 2015 in corresponding application No. PCT/JP2015/050722.
Chinese Office Action dated Jun. 23, 2017 issued in the corresponding Chinese patent application No. 201580004866.2 with its English Machine Translation.
David Hanss et al., "Cyclometalated Iridium(III) Complexes as Photosensitizers for Long-Range Electron Transfer: Occurrence of a Coulomb Barrier", Eur. J. Inorg. Chem, 2009, pp. 4850-4859.
Mathieu E. Walther et al., "Hole Tunneling and Hopping in a Ru(bpyh2+-Phenothiazine Dyad with a Bridge Derived from oligo-p-PhenyleneInorg", Inorg. Chem., 50, 2011, pp. 10901-10907.
David Hanss et al., "Conformational Effects on Long-Range Electron Transfer: Comparison of Oligo-p-phenylene and Oligo-p-xylene Bridges", Eur. J. Inorg. Chem., 2009, pp. 3776-3790.
David Hanss et al., "Tunneling Barrier Effects on Photoinduced Charge Transfer through Covalent Rigid Rod-Like Bridges", Inorg. Chem. 2009, 48, pp. 671-680.

LIGHT-EMITTING MATERIAL, ORGANIC LIGHT-EMITTING DEVICE, AND COMPOUND

TECHNICAL FIELD

The present invention relates to a compound that is useful as a light-emitting material, and an organic light-emitting device using the same.

BACKGROUND ART

An organic light-emitting device, such as an organic electroluminescent device (organic EL device), has been actively studied for enhancing the light emission efficiency thereof. In particular, various studies for enhancing the light-emitting efficiency have been made by newly developing an electron transporting material, a hole transporting material, a light-emitting material and the like constituting an organic electroluminescent device. There are studies relating to an organic electroluminescent device utilizing a compound having a structure having a cyclic structure containing a pyridine ring having bonded thereto a tertiary amino group.

PTL 1 proposes a phenanthroline derivative having introduced thereto tertiary amino groups NY and NY' represented by the following general formula. The literature describes that the phenanthroline derivatives having introduced thereto tertiary amino groups having a tricyclic structure, such as a phenoxazinyl group and a phenothiazinyl group, are confirmed for light emission characteristics.

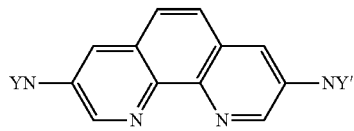

NPL 1 describes results of studies on light emission characteristics in the visible region and electrochemical characteristics of a phenanthroline derivative having introduced thereto a tertiary amino group, such as a phenoxazinyl group and a phenothiazinyl group.

CITATION LIST

Patent Literature

PTL 1: JP-A-2004-331586

Non-Patent Literature

NPL 1: Inorganica Chimica Acta, 357, (2004) 4335-4340

SUMMARY OF INVENTION

Technical Problem

As described above, PTL 1 and NPL 1 describe that a phenanthroline derivative having introduced thereto a tertiary amino group, such as a phenoxazinyl group, emits light in the visible region. As a result of actual evaluation by the present inventors on the light emission characteristics of the phenanthroline derivative having introduced thereto a tertiary amino group, however, it has been found that the light emission characteristics are not sufficiently satisfactory, and it is necessary to provide a light-emitting material having further excellent light emission characteristics.

Accordingly, the inventors have started various investigations on a group of compounds having a pyridine ring and a tertiary amino group, and have found that among numerous analogous structures, a group of compounds having a bipyridine structure having introduced thereto a tertiary amino group has usefulness as a light-emitting material, and the inventors have decided to perform further investigations. The light emission characteristics in the visible region of the compound having a phenanthroline structure have been confirmed by PTL 1 and NPL 1 as described above. However, the literatures do not describe a compound having a bipyridine structure having introduced thereto a tertiary amino group. Accordingly, it is completely unable to expect the usefulness as a light-emitting material of a compound having a bipyridine structure having introduced thereto a tertiary amino group.

Under the circumstances, the inventors have further performed investigations on the usefulness as a light-emitting material of a compound having a bipyridine structure having introduced thereto a tertiary amino group, and have accumulated studies for finding a compound excellent in light emission characteristics. The inventors have performed earnest investigations on the object of providing a general formula of compounds useful as a light-emitting material, and generalizing the structure of an organic light-emitting device having a high light emission efficiency.

Solution to Problem

As a result of the earnest investigations performed, the inventors have found that a bipyridine derivative having a particular structure has excellent properties as a light-emitting material. The inventors also have found that the group of compound includes a compound that is useful as a delayed fluorescent emitter, and have clarified that an organic light-emitting device having a high light emission efficiency can be provided inexpensively. The inventors thus have provided the following invention as a measure for solving the aforementioned problems based on the findings.

(1) A light-emitting material containing a compound represented by the following general formula (1):

General Formula (1)

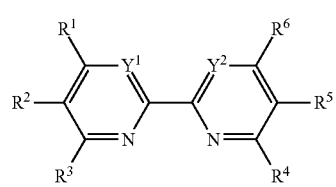

wherein in the general formula (1), $Y^1$ and $Y^2$ each independently represent N or $C(R^7)$; and $R^1$ to $R^7$ each independently represent a hydrogen atom or a substituent, provided that at least one of $R^1$ and $R^2$, and at least one of $R^5$ and $R^6$ each independently represent a group represented by the following general formula (2):

General Formula (2)

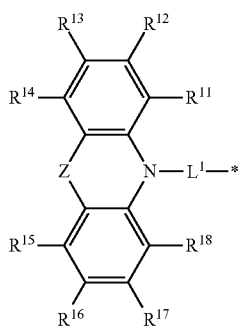

wherein in the general formula (2), Z represent a divalent linking group having a linking chain length of 1 atom; $L_1$ represents a single bond or a substituted or unsubstituted arylene group; * represents a position bonded to the heterocyclic ring in the general formula (1); and $R^{11}$ to $R^{18}$ each independently represent a hydrogen atom or a substituent, provided that $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ each may be bonded to each other to form a cyclic structure.

(2) The light-emitting material according to the item (1), wherein the group represented by the general formula (2) is a group represented by any one of the following general formulae (3) to (7):

General Formula (3)

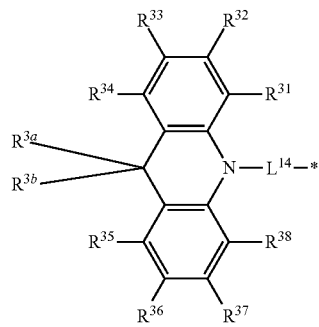

General Formula (4)

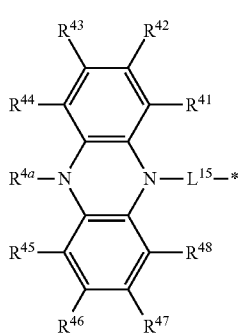

General Formula (5)

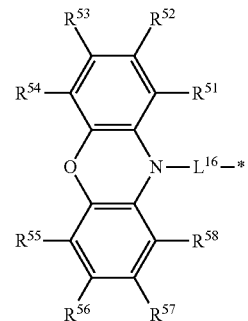

General Formula (6)

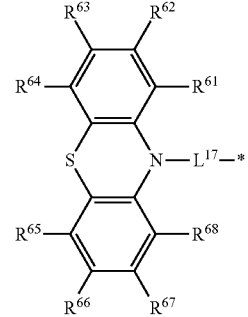

General Formula (7)

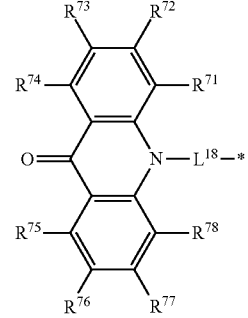

wherein in the general formulae (3) to (7), $L^{14}$ to $L^{18}$ each represent a single bond or a substituted or unsubstituted arylene group; * represents a position bonded to the heterocyclic ring in the general formula (1); and $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each independently represent a hydrogen atom or a substituent, provided that $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may be bonded to each other to form a cyclic structure.

(3) The light-emitting material according to the item (1) or (2), wherein in the general formula (1), $R^2$ and $R^5$ each independently represent a group represented by the general formula (2).

(4) The light-emitting material according to any one of the items (1) to (3), wherein in the general formula (1), $Y^1$ and $Y^2$ both represent N or both represent $C(R^7)$.

(5) The light-emitting material according to any one of the items (1) to (4), wherein in the general formula (2), $L^1$ represents a single bond.

(6) The light-emitting material according to any one of the items (1) to (5), wherein all the groups represented by the general formula (2) present in a molecule of the compound are the same as each other.

(7) The light-emitting material according to any one of the items (1) to (6), wherein a molecule of the compound has a rotationally symmetric structure.

(8) The light-emitting material according to any one of the items (1) to (6), wherein a molecule of the compound has an axisymmetric structure.

(9) A delayed fluorescent emitter containing a compound represented by the general formula (1).

(10) An organic light-emitting device containing the light-emitting material according to any one of the items (1) to (8).

(11) The organic light-emitting device according to the item (10), wherein the organic light-emitting device emits delayed fluorescent light.

(12) The organic light-emitting device according to the item (10) or (11), wherein the organic light-emitting device is an organic electroluminescent device.

(13) A compound represented by the following general formula (1'):

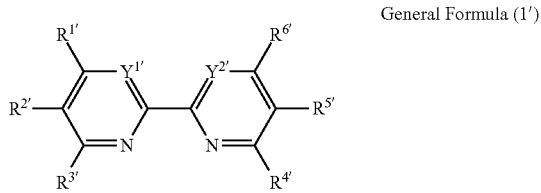

General Formula (1')

wherein in the general formula (1'), $Y^{1'}$ and $Y^{2'}$ each independently represent N or $C(R^{7'})$; and $R^{1'}$ to $R^{7'}$ each independently represent a hydrogen atom or a substituent, provided that at least one of $R^{1'}$ and $R^{2'}$, and at least one of $R^{5'}$ and $R^{6'}$ each independently represent a group represented by the following general formula (2'):

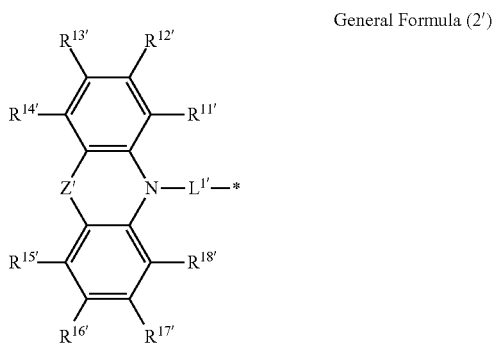

General Formula (2')

wherein in the general formula (2'), Z' represent a divalent linking group having a linking chain length of 1 atom; $L^{1'}$ represents a single bond or a substituted or unsubstituted arylene group; * represents a position bonded to the heterocyclic ring in the general formula (1'); and $R^{11'}$ to $R^{18'}$ each independently represent a hydrogen atom or a substituent, provided that $R^{11'}$ and $R^{12'}$, $R^{12'}$ and $R^{13'}$, $R^{13'}$ and $R^{14'}$, $R^{15'}$ and $R^{16'}$, $R^{16'}$ and $R^{17'}$, and $R^{17'}$ and $R^{18'}$ each may be bonded to each other to form a cyclic structure.

Advantageous Effects of Invention

The compound of the invention is useful as a light-emitting material. The compound of the invention includes one that emits delayed fluorescent light. The organic light-emitting device using the compound of the invention as a light-emitting material is capable of achieving a high light emission efficiency.

DESCRIPTION OF EMBODIMENTS

Figure 1:
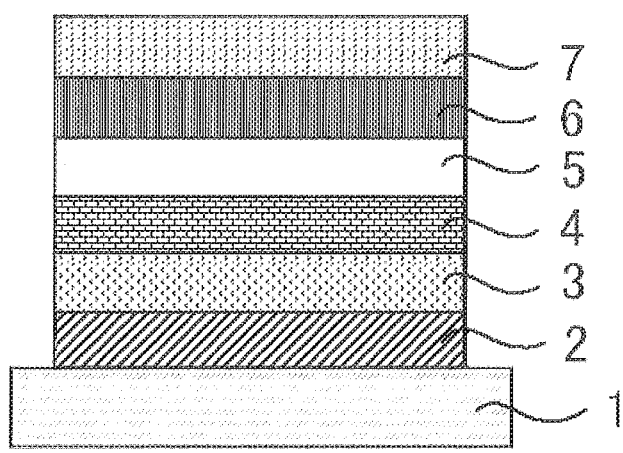
FIG. 1 is a schematic cross sectional view showing an example of a layer structure of an organic electroluminescent device.

The contents of the invention will be described in detail below. The constitutional elements may be described below with reference to representative embodiments and specific examples of the invention, but the invention is not limited to the embodiments and the examples. In the description, a numerical range expressed with reference to an upper limit and/or a lower limit means a range that includes the upper limit and/or the lower limit. In the invention, the hydrogen atom that is present in the molecule of the compound used in the invention is not particularly limited in isotope species, and for example, all the hydrogen atoms in the molecule may be $^1H$, and all or a part of them may be $^2H$ (deuterium (D)).

Compound Represented by General Formula (1)

The light-emitting material of the invention contains a compound represented by the following general formula (1):

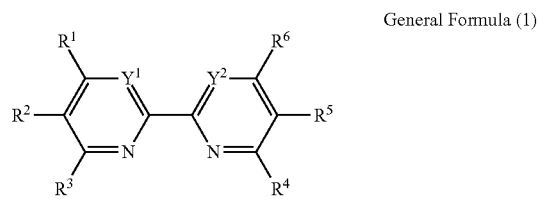

General Formula (1)

In the general formula (1), $Y^1$ and $Y^2$ each independently represent N or $C(R^7)$. One of $Y^1$ and $Y^2$ may represent N, whereas the other thereof may represent $C(R^7)$, and $Y^1$ and $Y^2$ both may represent N or both may represent $C(R^7)$. It is preferred that $Y^1$ and $Y^2$ both represent N or both represent $C(R^7)$, and it is more preferred that $Y^1$ and $Y^2$ both represent $C(R^7)$.

$R^1$ to $R^7$ each independently represent a hydrogen atom or a substituent, provided that at least one of $R^1$ and $R^2$, and at least one of $R^5$ and $R^6$ each independently represent a group represented by the following general formula (2). The group represented by the following general formula (2) may be any one of $R^1$ and $R^2$ and may be both $R^1$ and $R^2$, and is preferably any one of $R^1$ and $R^2$. The group represented by the general formula (2) may be any one of $R^5$ and $R^6$ and may be both $R^5$ and $R^6$, and is preferably any one of $R^5$ and $R^6$. The number of the group represented by the general formula (2) in $R^1$ and $R^2$ and the number of the group represented by the general formula (2) in $R^5$ and $R^6$ may be the same as or different from each other, and are preferably the same as each other. Preferred examples of the compound include a compound represented by the general formula (1), in which $R^1$ and $R^6$ each represent a group represented by the general formula (2), and a compound represented by the general formula (1), in which $R^2$ and $R^5$ each represent a group represented by the general formula (2), and more preferred examples of the compound include a compound represented by the general formula (1), in which $R^2$ and $R^5$ each represent a group represented by the general formula (2). The plural groups each represented by the general formula (2) present in the general formula (1) may be the same as or different from each other, and are preferably the same as each other. The compound represented by the general formula (1) preferably has a rotationally symmetric structure. Specifically, it is preferred that $Y^1$ and $Y^2$ represent N, and $R^1$ and $R^4$, $R^2$ and $R^5$, and $R^3$ and $R^6$ each are the same as each other. The compound represented by the general formula (1) preferably has an axisymmetric structure. Specifically, it is preferred that $Y^1$ and $Y^2$, $R^1$ and $R^6$, $R^2$ and $R^5$, and $R^3$ and $R^4$ each are the same as each other.

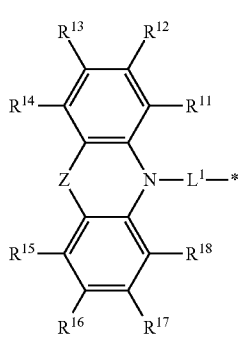

General Formula (2)

In the general formula (2), Z represents a divalent linking group having a linking chain length of 1 atom. The linking group is not particularly limited as far as the group has a linking chain length of 1 atom. Preferred examples of the linking group include a linking group, in which the atom bonded to C of the benzene rings is C, N, O, or S, and more preferred examples of the linking group include $C(R^{3a})(R^{3b})$, $C=O$, $N(R^{4a})$, O, and S, in which $R^{3a}$, $R^{3b}$, and $R^{4a}$ have the same meanings as $R^{3a}$ and $R^{3b}$ in the following general formula (3) and $R^{4a}$ in the general formula (4), respectively.

$L^1$ represents a single bond or a substituted or unsubstituted arylene group, and preferably represents a single bond. * represents a position bonded to the heterocyclic ring in the general formula (1). In the case where $L^1$ represents an arylene group, the arylene group is preferably an arylene group having from 6 to 18 carbon atoms. Examples of the arylene group having from 6 to 18 carbon atoms include a phenylene group, a biphenylene group, a fluorenylene group, and a triphenylenylene group, more preferred examples of the linking group is a phenylene group, and further preferred examples of the linking group include a 1,4-phenylene group. For the description and the preferred range of the substituent in the case where the arylene group has the substituent, reference may be made to the description and the preferred range of the substituent that may be represented by $R^1$ to $R^7$ and the like.

In the general formula (2), $R^{11}$ to $R^{18}$ each independently represent a hydrogen atom or a substituent. The number of the substituent is not particularly limited, and all $R^{11}$ to $R^{18}$ may be unsubstituted (i.e., hydrogen atoms). In the case where 2 or more of $R^{11}$ to $R^{18}$ each represent a substituent, the plural substituents may be the same as or different from each other.

Examples of the substituent that may be represented by $R^{11}$ to $R^{18}$ and examples of the substituent that may be represented by $R^1$ to $R^7$ include a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms, and a nitro group. In these specific examples, the substituent that is capable of being further substituted with a substituent may be substituted. More preferred examples of the substituent include a halogen atom, a cyano group, a substituted or unsubstituted alkyl group having from 1 to 20 carbon atoms, an alkoxy group having from 1 to 20 carbon atoms, a substituted or unsubstituted aryl group having from 6 to 40 carbon atoms, a substituted or unsubstituted heteroaryl group having from 3 to 40 carbon atoms, and a dialkyl-substituted amino group having from 2 to 20 carbon atoms. Further preferred examples of the substituent include a fluorine atom, a chlorine atom, a cyano group, a substituted or unsubstituted alkyl group having from 1 to 10 carbon atoms, a substituted or unsubstituted alkoxy group having from 1 to 10 carbon atoms, a substituted or unsubstituted aryl group having from 6 to 15 carbon atoms, and a substituted or unsubstituted heteroaryl group having from 3 to 12 carbon atoms.

$R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ each may be bonded to each other to form a cyclic structure. The cyclic structure may be an aromatic ring or an aliphatic ring, and may be one containing a hetero atom, and the cyclic structure may also be a condensed ring containing 2 or more rings. The hetero atom herein is preferably selected from the group consisting of a nitrogen atom, an oxygen atom and a sulfur atom. Examples of the cyclic structure formed include a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring and a cycloheptene ring.

The group represented by the general formula (2) is preferably a group represented by any one of the following general formulae (3) to (7):

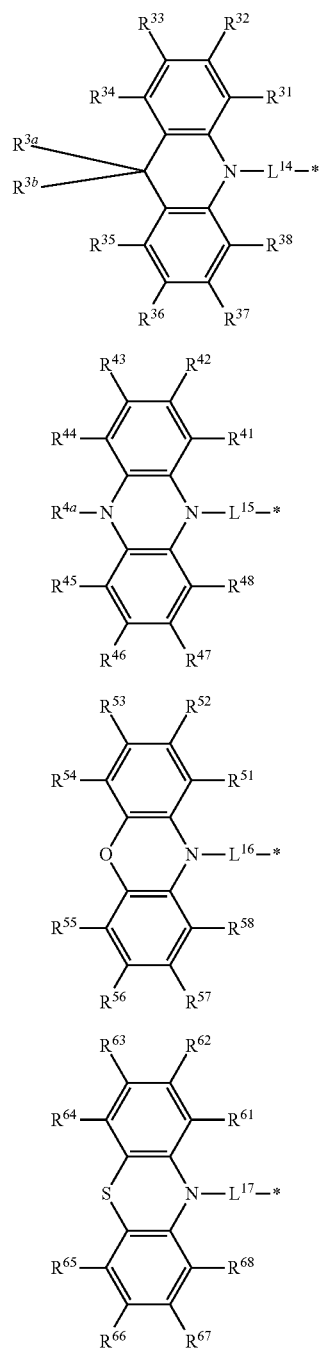

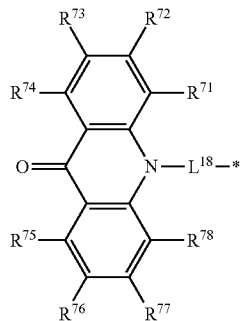

In the general formulae (3) to (7), $L^{14}$ to $L^{18}$ each represent a single bond or a substituted or unsubstituted arylene group; and * represents a position bonded to the heterocyclic ring in the general formula (1). In the case where $L^{14}$ to $L^{18}$ each represent an arylene group, for the description and the preferred range of the arylene group, reference may be made to the description and the preferred range of the arylene group in the case where $L^1$ represents an arylene group.

$R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each independently represent a hydrogen atom or a substituent. The description and the preferred range of the substituent herein, reference may be made to the description and the preferred range of the substituent that may be represented by $R^1$ to $R^7$ and the like. $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each preferably independently represent a group represented by any one of the following general formulae (3) to (7). The number of the substituent in the general formulae (3) to (7) is not particularly limited. The case where all are not substituted (i.e., hydrogen atoms) is also preferred. $R^{3a}$ and $R^{3b}$ each preferably represent a substituted or unsubstituted alkyl group or a substituted or unsubstituted aryl group, and each more preferably represent a substituted or unsubstituted alkyl group having from 1 to 6 carbon atoms or a substituted or unsubstituted aryl group having from 6 to 18 carbon atoms. In the case where 2 or more substituents are present in each of the general formulae (3) to (7), the substituents may be the same as or different from each other. In the case where a substituent is present in the general formulae (3) to (7), the substituent is preferably any of $R^{32}$ to $R^{37}$, $R^{3a}$, and $R^{3b}$, and more preferably at least one of $R^{3a}$ and $R^{3b}$ for the general formula (3); preferably any of $R^{42}$ to $R^{47}$ and $R^{4a}$ for the general formula (4); preferably any of $R^{52}$ to $R^{57}$ for the general formula (5); preferably any of $R^{62}$ to $R^{67}$ for the general formula (6); and preferably any of $R^{72}$ to $R^{77}$ for the general formula (7).

In the general formula (3) to (7), $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may be bonded to each other to form a cyclic structure. For the description and the preferred examples of the cyclic structure, reference may be made to the description and the preferred examples of the cyclic structure that is formed by bonding $R^{11}$ and $R^{12}$, and the like in the general formula (2).

All the groups each represented by the general formula (2) present in the general formula (1) are preferably groups represented by any one of the general formulae (3) to (7). Examples of the case include a case where all the groups are groups represented by the general formula (5).

Specific examples of the compound represented by the general formula (1) are shown below. However, the compound represented by the general formula (1) capable of being used in the invention is not construed as being limited to the specific examples. In the following formulae, Me represents a methyl group.

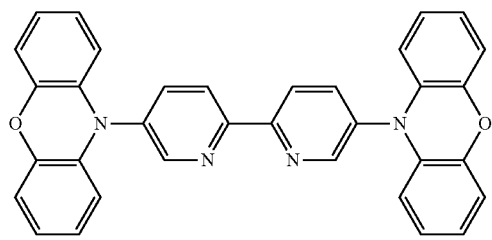

1

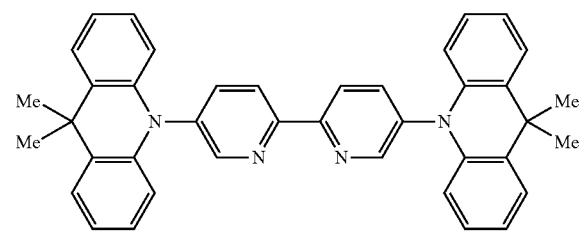

2

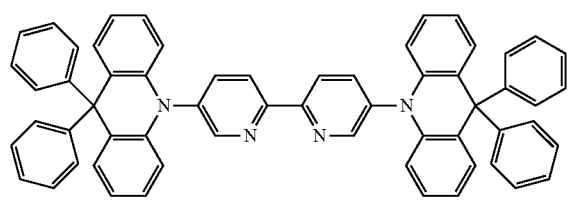

3

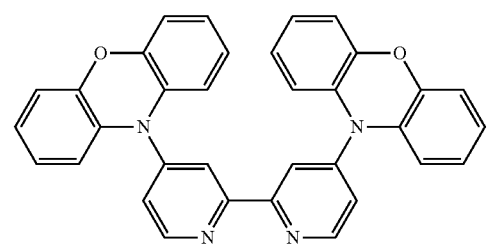

4

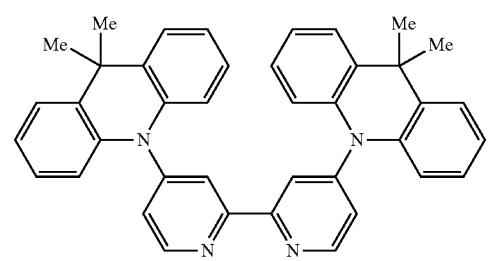

5

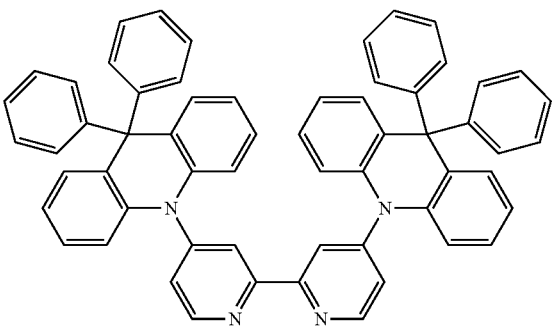

6

The molecular weight of the compound represented by the general formula (1) is preferably 1,500 or less, more preferably 1,200 or less, further preferably 1,000 or less, and still further preferably 800 or less, for example, in the case where an organic layer containing the compound represented by the general formula (1) is intended to be formed as a film by a vapor deposition method. The lower limit of the molecular weight is the molecular weight of the smallest compound represented by the general formula (1).

The compound represented by the general formula (1) may be formed into a film by a coating method irrespective of the molecular weight thereof. The compound that has a relatively large molecular weight may be formed into a film by a coating method.

As an application of the invention, it may be considered that a compound that contains plural structures each represented by the general formula (1) in the molecule is used as a light-emitting material.

For example, it may be considered that a polymerizable group is introduced in advance to the structure represented by the general formula (1), and a polymer obtained by polymerizing the polymerizable group is used as a light-emitting material. Specifically, it may be considered that a monomer that has a polymerizable functional group at any of $R^1$ to $R^7$ in the general formula (1) is prepared, and is homopolymerized or copolymerized with another monomer to prepare a polymer containing repeating units, and the polymer is used as a light-emitting material. In alternative, it may be considered that the compounds having the structure represented by the general formula (1) are reacted to form a dimer or a trimer, and the dimer or the trimer is used as a light-emitting material.

Examples of the polymer having the repeating unit containing the structure represented by the general formula (1) include a polymer containing a structure represented by the following general formula (8) or (9).

General Formula (8)

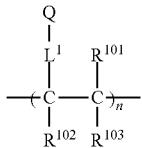

General Formula (9)

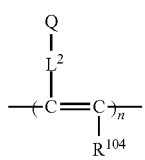

In the general formulae (8) and (9), Q represents a group containing the structure represented by the general formula (1), and $L^1$ and $L^2$ each represent a linking group. The linking group preferably has from 0 to 20 carbon atoms, more preferably from 1 to 15 carbon atoms, and further preferably from 2 to 10 carbon atoms. The linking group preferably has a structure represented by $-X^{11}\text{-}L^{11}\text{-}$, wherein $X^{11}$ represents an oxygen atom or a sulfur atom, and preferably an oxygen atom, and $L^{11}$ represents a linking group, preferably a substituted or unsubstituted alkylene group or a substituted or unsubstituted arylene group, and more preferably a substituted or unsubstituted alkylene group having from 1 to 10 carbon atoms or a substituted or unsubstituted phenylene group.

In the general formulae (8) and (9), $R^{101}$, $R^{102}$, $R^{103}$ and $R^{104}$ each independently represent a substituent, preferably a substituted or unsubstituted alkyl group having from 1 to 6 carbon atoms, a substituted or unsubstituted alkoxy group having from 1 to 6 carbon atoms, or a halogen atom, more preferably an unsubstituted alkyl group having from 1 to 3 carbon atoms, an unsubstituted alkoxy group having from 1 to 3 carbon atoms, a fluorine atom or a chlorine atom, and further preferably an unsubstituted alkyl group having from 1 to 3 carbon atoms or an unsubstituted alkoxy group having from 1 to 3 carbon atoms.

The linking group represented by $L^1$ and $L^2$ may be bonded to any of $R^1$ to $R^7$ of the structure of the general formula (1) constituting Q, any of $R^{11}$ to $R^{18}$ of the structure of the general formula (2), any of $R^{31}$ to $R^{38}$, $R^{3a}$, and $R^{3b}$ of the structure of the general formula (3), any of $R^{41}$ to $R^{48}$ and $R^{4a}$ of the structure of the general formula (4), any of $R^{51}$ to $R^{58}$ of the structure of the general formula (5), any of $R^{61}$ to $R^{68}$ of the structure of the general formula (6), and any of $R^{71}$ to $R^{78}$ of the structure of the general formula (7). Two or more of the linking groups may be boded to one group represented by Q to form a crosslinked structure or a network structure.

Specific examples of the structure of the repeating unit include structures represented by the following formulae (10) to (13).

Formula (10)

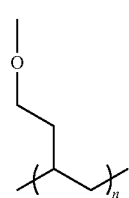

Formula (11)

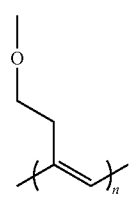

Formula (12)

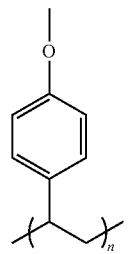

Formula (13)

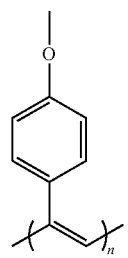

The polymer having the repeating unit containing the structure represented by any of the formulae (10) to (13) may be synthesized in such a manner that a hydroxyl group is introduced to any of $R^1$ to $R^7$ in the structure represented by the general formula (1), and the hydroxyl group as a linker is reacted with the following compound to introduce a polymerizable group thereto, followed by polymerizing the polymerizable group.

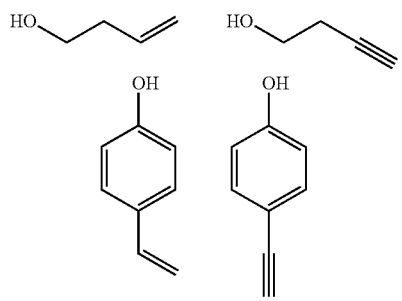

The polymer containing the structure represented by the general formula (1) in the molecule may be a polymer containing only a repeating unit having the structure represented by the general formula (1), or a polymer further containing a repeating unit having another structure. The repeating unit having the structure represented by the general formula (1) contained in the polymer may be only one kind or two or more kinds. Examples of the repeating unit that does not have the structure represented by the general formula (1) include a repeating unit derived from a monomer that is used for ordinary copolymerization. Examples of the repeating unit include a repeating unit derived from a monomer having an ethylenic unsaturated bond, such as ethylene and styrene.

Compound Represented by General Formula (1')

The compound represented by the general formula (1') is a novel compound.

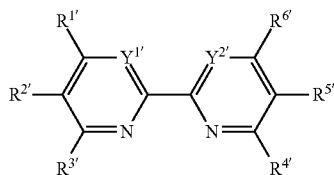

General Formula (1')

In the general formula (1'), $Y^{1'}$ and $Y^{2'}$ each independently represent N or C($R^{7'}$); and $R^{1'}$ to $R^{7'}$ each independently represent a hydrogen atom or a substituent, provided that at least one of $R^{1'}$ and $R^{2'}$, and at least one of $R^{5'}$ and $R^{6'}$ each independently represent a group represented by the following general formula (2').

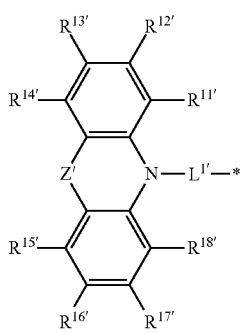

General Formula (2')

In the general formula (2'), Z' represent a divalent linking group having a linking chain length of 1 atom; $L^{1'}$ represents a single bond or a substituted or unsubstituted arylene group; * represents a position bonded to the heterocyclic ring in the general formula (1'); and $R^{11'}$ to $R^{18'}$ each independently represent a hydrogen atom or a substituent, provided that $R^{11'}$ and $R^{12'}$, $R^{12'}$ and $R^{13'}$, $R^{13'}$ and $R^{14'}$, $R^{15'}$ and $R^{16'}$, $R^{16'}$ and $R^{17'}$, and $R^{17'}$ and $R^{18'}$ each may be bonded to each other to form a cyclic structure.

For the descriptions and the preferred ranges of $Y^{1'}$, $Y^{2'}$, $R^{1'}$ to $R^{7'}$, Z', $L^{1'}$, and $R^{11'}$ to $R^{18'}$, reference may be made to the descriptions for the compound represented by the general formula (1).

Synthesis Method of Compound Represented by General Formula (1')

The compound represented by the general formula (1') may be synthesized by combining the known reactions. For example, a compound represented by the general formula (1'), in which $R^{2'}$ and $R^{5'}$ each represent a group represented by the general formula (2'), can be synthesized by reacting the following two compounds.

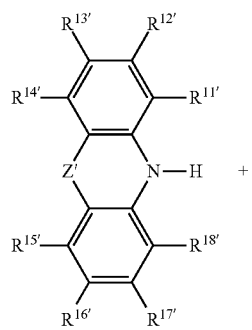

2

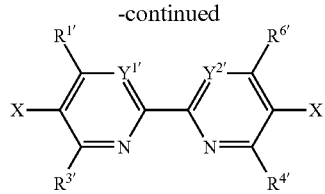

-continued

For the descriptions of $R^{1'}$, $R^{3'}$, $R^{4'}$, $R^{6'}$, and $R^{11'}$ to $R^{18'}$ in the aforementioned reaction scheme, reference may be made to the corresponding descriptions for the general formula (1'). X represents a halogen atom, examples of which include a fluorine atom, a chlorine atom, a bromine atom, and an iodine atom, and a chlorine atom, a bromine atom, and an iodine atom are preferred.

The reaction in the aforementioned reaction scheme is an application of the known reaction, such as the Ullmann reaction and the Buchwald-Hartwig reaction, and the known reaction conditions may be appropriately selected and used. For the details of the reactions, reference may be made to the synthesis examples described later. The compound represented by the general formula (1') may also be synthesized by combining the other known synthesis reactions.

The dibromide of bipyridine and the amine derivative used as the intermediates may be commercially available products or may be compounds synthesized. The dibromide of bipyridine can be synthesized, for example, by the method described in Tetrahedron Letters, 36(36), 6471-4 (1995). The amine derivative can be synthesized, for example, by the method described in Journal of Organic Chemistry, 76(9), 2976-2993 (2011).

Organic Light-Emitting Device

The compound represented by the general formula (1) of the invention is useful as a light-emitting material of an organic light-emitting device. Accordingly, the compound represented by the general formula (1) of the invention may be effectively used as a light-emitting material in a light-emitting layer of an organic light-emitting device. The compound represented by the general formula (1) includes a delayed fluorescent material emitting delayed fluorescent light (delayed fluorescent emitter). Thus, the invention provides an invention relating to a delayed fluorescent emitter having the structure represented by the general formula (1), an invention relating to the use of the compound represented by the general formula (1) as the delayed fluorescent emitter, and an invention relating to a method for emitting delayed fluorescent light with the compound represented by the general formula (1). An organic light-emitting device that uses the compound as a light-emitting material has features that the device emits delayed fluorescent light and has a high light emission efficiency. The principle of the features may be described as follows for an organic electroluminescent device as an example.

In an organic electroluminescent device, carriers are injected from an anode and a cathode to a light-emitting material to form an excited state for the light-emitting material, with which light is emitted. In the case of a carrier injection type organic electroluminescent device, in general, excitons that are excited to the excited singlet state are 25% of the total excitons generated, and the remaining 75% thereof are excited to the excited triplet state. Accordingly, the use of phosphorescence, which is light emission from the excited triplet state, provides a high energy utilization. However, the excited triplet state has a long lifetime and thus causes saturation of the excited state and deactivation of energy through mutual action with the excitons in the excited triplet state, and therefore the quantum yield of phosphorescence may generally be often not high. A delayed fluorescent material emits fluorescent light through the mechanism that the energy of excitons transits to the excited triplet state through intersystem crossing or the like, and then transits to the excited singlet state through reverse intersystem crossing due to triplet-triplet annihilation or absorption of thermal energy, thereby emitting fluorescent light. It is considered that among the materials, a thermal activation type delayed fluorescent material emitting light through absorption of thermal energy is particularly useful for an organic electroluminescent device. In the case where a delayed fluorescent material is used in an organic electroluminescent device, the excitons in the excited singlet state normally emit fluorescent light. On the other hand, the excitons in the excited triplet state emit fluorescent light through intersystem crossing to the excited singlet state by absorbing the heat generated by the device. At this time, the light emitted through reverse intersystem crossing from the excited triplet state to the excited singlet state has the same wavelength as fluorescent light since it is light emission from the excited singlet state, but has a longer lifetime (light emission lifetime) than the normal fluorescent light and phosphorescent light, and thus the light is observed as fluorescent light that is delayed from the normal fluorescent light and phosphorescent light. The light may be defined as delayed fluorescent light. The use of the thermal activation type exciton transition mechanism may raise the proportion of the compound in the excited singlet state, which is generally formed in a proportion only of 25%, to 25% or more through the absorption of the thermal energy after the carrier injection. A compound that emits strong fluorescent light and delayed fluorescent light at a low temperature of lower than 100° C. undergoes the intersystem crossing from the excited triplet state to the excited singlet state sufficiently with the heat of the device, thereby emitting delayed fluorescent light, and thus the use of the compound may drastically enhance the light emission efficiency, where light emission efficiency is defined and hereafter used for mean photoluminescence quantum efficiency, electroluminescence quantum efficiency, or both as appropriate.

The use of the compound represented by the general formula (1) of the invention as a light-emitting material of a light-emitting layer may provide an excellent organic light-emitting device, such as an organic photoluminescent device (organic PL device) and an organic electroluminescent device (organic EL device). At this time, the compound represented by the general formula (1) of the invention may have a function of assisting light emission of another light-emitting material contained in the light-emitting layer, i.e., as a so-called assist dopant. Specifically, the compound represented by the general formula (1) of the invention contained in the light-emitting layer may have a lowest excited singlet energy level that is between the lowest excited singlet energy level of the host material contained in the light-emitting layer and the lowest excited singlet energy level of the another light-emitting material contained in the light-emitting layer.

The organic photoluminescent device has a structure containing a substrate having formed thereon at least a light-emitting layer. The organic electroluminescent device has a structure containing at least an anode, a cathode and an organic layer formed between the anode and the cathode. The organic layer contains at least a light-emitting layer, and may be formed only of a light-emitting layer, or may have one or more organic layer in addition to the light-emitting layer. Examples of the organic layer include a hole transporting layer, a hole injection layer, an electron barrier layer, a hole barrier layer, an electron injection layer, an electron transporting layer and an exciton barrier layer. The hole transporting layer may be a hole injection and transporting layer having a hole injection function, and the electron transporting layer may be an electron injection and transporting layer having an electron injection function. A specific structural example of an organic electroluminescent device is shown in FIG. 1. In FIG. 1, the numeral 1 denotes a substrate, 2 denotes an anode, 3 denotes a hole injection layer, 4 denotes a hole transporting layer, 5 denotes a light-emitting layer, 6 denotes an electron transporting layer, and 7 denotes a cathode.

The members and the layers of the organic electroluminescent device will be described below. The descriptions for the substrate and the light-emitting layer may also be applied to the substrate and the light-emitting layer of the organic photoluminescent device.

Substrate

The organic electroluminescent device of the invention is preferably supported by a substrate. The substrate is not particularly limited and may be those that have been commonly used in an organic electroluminescent device, and examples thereof which may be used include those formed of glass, transparent plastics, quartz and silicon.

Anode

The anode of the organic electroluminescent device used is preferably formed of as an electrode material a metal, an alloy or an electroconductive compound each having a large work function (4 eV or more), or a mixture thereof. Specific examples of the electrode material include a metal, such as Au, and an electroconductive transparent material, such as CuI, indium tin oxide (ITO), $SnO_2$ and ZnO. A material that is amorphous and is capable of forming a transparent electroconductive film, such as IDIXO ($In_2O_3$—ZnO), may also be used. The anode may be formed in such a manner that the electrode material is formed into a thin film by such a method as vapor deposition or sputtering, and the film is patterned into a desired pattern by a photolithography method, or in the case where the pattern may not require high accuracy (for example, approximately 100 μm or more), the pattern may be formed with a mask having a desired shape on vapor deposition or sputtering of the electrode material. In alternative, in the case where a material capable of being applied as a coating, such as an organic electroconductive compound, is used, a wet film forming method, such as a printing method and a coating method, may be used. In the case where emitted light is to be taken out through the anode, the anode preferably has a transmittance of more than 10%, and the anode preferably has a sheet resistance of several hundred Ohm per square or less. The thickness thereof may be generally selected from a range of from 10 to 1,000 nm, and preferably from 10 to 200 nm, while depending on the material used.

Cathode

The cathode is preferably formed of as an electrode material a metal having a small work function (4 eV or less) (referred to as an electron injection metal), an alloy or an electroconductive compound each having a small work function (4 eV or less), or a mixture thereof. Specific examples of the electrode material include sodium, a sodium-potassium alloy, magnesium, lithium, a magnesium-copper mixture, a magnesium-silver mixture, a magnesium-aluminum mixture, a magnesium-indium mixture, an aluminum-aluminum oxide ($Al_2O_3$) mixture, indium, a lithium-aluminum mixture, and a rare earth metal. Among these, a mixture of an electron injection metal and a second metal that is a stable metal having a larger work function than the electron injection metal, for example, a magnesium-silver mixture, a magnesium-aluminum mixture, a magnesium-indium mixture, an aluminum-aluminum oxide ($Al_2O_3$) mixture, a lithium-aluminum mixture, and aluminum, are preferred from the standpoint of the electron injection property and the durability against oxidation and the like. The cathode may be produced by forming the electrode material into a thin film by such a method as vapor deposition or sputtering. The cathode preferably has a sheet resistance of several hundred Ohm per square or less, and the thickness thereof may be generally selected from a range of from 10 nm to 5 μm, and preferably from 50 to 200 nm. For transmitting the emitted light, any one of the anode and the cathode of the organic electroluminescent device is preferably transparent or translucent, thereby enhancing the light emission luminance.

The cathode may be formed with the electroconductive transparent materials described for the anode, thereby forming a transparent or translucent cathode, and by applying the cathode, a device having an anode and a cathode, both of which have transmittance, may be produced.

Light-Emitting Layer

The light-emitting layer is a layer, in which holes and electrons injected from the anode and the cathode, respectively, are recombined to form excitons, and then the layer emits light. A light-emitting material may be solely used as the light-emitting layer, but the light-emitting layer preferably contains a light-emitting material and a host material. The light-emitting material used may be one kind or two or more kinds selected from the group of compounds represented by the general formula (1) of the invention. In order that the organic electroluminescent device and the organic photoluminescent device of the invention exhibit a high light emission efficiency, it is important that the singlet excitons and the triplet excitons generated in the light-emitting material are confined in the light-emitting material. Accordingly, a host material is preferably used in addition to the light-emitting material in the light-emitting layer. The host material used may be an organic compound that has excited singlet energy and excited triplet energy, at least one of which is higher than those of the light-emitting material of the invention. As a result, the singlet excitons and the triplet excitons generated in the light-emitting material of the invention are capable of being confined in the molecules of the light-emitting material of the invention, thereby eliciting the light emission efficiency thereof sufficiently. Even though the singlet excitons and the triplet excitons are not confined sufficiently, a high light emission efficiency may be obtained in some cases, and thus a host material that is capable of achieving a high light emission efficiency may be used in the invention without any particular limitation. In the organic light-emitting device and the organic electroluminescent device of the invention, the light emission occurs in the light-emitting material of the invention contained in the light-emitting layer. The emitted light contains both fluorescent light and delayed fluorescent light. However, a part of the emitted light may contain emitted light from the host material, or the emitted light may partially contain emitted light from the host material.

In the case where the host material is used, the amount of the compound of the invention as the light-emitting material contained in the light-emitting layer is preferably 0.1% by weight or more, and more preferably 1% by weight or more, and is preferably 50% by weight or less, more preferably 20% by weight or less, and further preferably 10% by weight or less.

The host material in the light-emitting layer is preferably an organic compound that has a hole transporting function and an electron transporting function, prevents the emitted light from being increased in wavelength, and has a high glass transition temperature.

Injection Layer

The injection layer is a layer that is provided between the electrode and the organic layer, for decreasing the driving voltage and enhancing the light emission luminance, and includes a hole injection layer and an electron injection layer, which may be provided between the anode and the light-emitting layer or the hole transporting layer and between the cathode and the light-emitting layer or the electron transporting layer. The injection layer may be provided depending on necessity.

Barrier Layer

The barrier layer is a layer that is capable of inhibiting charges (electrons or holes) and/or excitons present in the light-emitting layer from being diffused outside the light-emitting layer. The electron barrier layer may be disposed between the light-emitting layer and the hole transporting layer, and inhibits electrons from passing through the light-emitting layer toward the hole transporting layer. Similarly, the hole barrier layer may be disposed between the light-emitting layer and the electron transporting layer, and inhibits holes from passing through the light-emitting layer toward the electron transporting layer. The barrier layer may also be used for inhibiting excitons from being diffused outside the light-emitting layer. Thus, the electron barrier layer and the hole barrier layer each may also have a function as an exciton barrier layer. The term "the electron barrier layer" or "the exciton barrier layer" referred herein is intended to include a layer that has both the functions of an electron barrier layer and an exciton barrier layer by one layer.

Hole Barrier Layer

The hole barrier layer has the function of an electron transporting layer in a broad sense. The hole barrier layer has a function of inhibiting holes from reaching the electron transporting layer while transporting electrons, and thereby enhances the recombination probability of electrons and holes in the light-emitting layer. As the material for the hole barrier layer, the materials for the electron transporting layer described later may be used depending on necessity.

Electron Barrier Layer

The electron barrier layer has the function of transporting holes in a broad sense. The electron barrier layer has a function of inhibiting electrons from reaching the hole transporting layer while transporting holes, and thereby enhances the recombination probability of electrons and holes in the light-emitting layer.

Exciton Barrier Layer

The exciton barrier layer is a layer for inhibiting excitons generated through recombination of holes and electrons in the light-emitting layer from being diffused to the charge transporting layer, and the use of the layer inserted enables effective confinement of excitons in the light-emitting layer, and thereby enhances the light emission efficiency of the device. The exciton barrier layer may be inserted adjacent to the light-emitting layer on any of the side of the anode and the side of the cathode, and on both the sides. Specifically, in the case where the exciton barrier layer is present on the side of the anode, the layer may be inserted between the hole transporting layer and the light-emitting layer and adjacent to the light-emitting layer, and in the case where the layer is inserted on the side of the cathode, the layer may be inserted between the light-emitting layer and the cathode and adjacent to the light-emitting layer. Between the anode and the exciton barrier layer that is adjacent to the light-emitting layer on the side of the anode, a hole injection layer, an electron barrier layer and the like may be provided, and between the cathode and the exciton barrier layer that is adjacent to the light-emitting layer on the side of the cathode, an electron injection layer, an electron transporting layer, a hole barrier layer and the like may be provided. In the case where the barrier layer is provided, the material used for the barrier layer preferably has excited singlet energy and excited triplet energy, at least one of which is higher than the excited singlet energy and the excited triplet energy of the light-emitting layer, respectively.

Hole Transporting Layer

The hole transporting layer is formed of a hole transporting material having a function of transporting holes, and the hole transporting layer may be provided as a single layer or plural layers.

The hole transporting material has one of injection or transporting property of holes and barrier property of electrons, and may be any of an organic material and an inorganic material. Examples of known hole transporting materials that may be used herein include a triazole derivative, an oxadiazole derivative, an imidazole derivative, a carbazole derivative, an indolocarbazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline copolymer and an electroconductive polymer oligomer, particularly a thiophene oligomer. Among these, a porphyrin compound, an aromatic tertiary amine compound and a styrylamine compound are preferably used, and an aromatic tertiary amine compound is more preferably used.

Electron Transporting Layer

The electron transporting layer is formed of a material having a function of transporting electrons, and the electron transporting layer may be provided as a single layer or plural layers.

The electron transporting material (which may also function as a hole barrier material in some cases) needs only to have a function of transporting electrons, which are injected from the cathode, to the light-emitting layer. Examples of the electron transporting layer that may be used herein include a nitro-substituted fluorene derivative, a diphenylquinone derivative, a thiopyran dioxide derivative, carbodiimide, a fluorenylidene methane derivative, anthraquinodimethane and anthrone derivatives, and an oxadiazole derivative. The electron transporting material used may be a thiadiazole derivative obtained by replacing the oxygen atom of the oxadiazole ring of the oxadiazole derivative by a sulfur atom, or a quinoxaline derivative having a quinoxaline ring, which is known as an electron attracting group. Furthermore, polymer materials having these materials introduced to the polymer chain or having these materials used as the main chain of the polymer may also be used.

In the production of the organic electroluminescent device, the compound represented by the general formula (1) may be used not only in the light-emitting layer but also in the other layers than the light-emitting layer. In this case, the compound represented by the general formula (1) used in the light-emitting layer and the compound represented by the general formula (1) used in the other layers than the light-emitting layer may be the same as or different from each other. For example, the compound represented by the general formula (1) may be used in the injection layer, the barrier layer, the hole barrier layer, the electron barrier layer, the exciton barrier layer, the hole transporting layer, the electron transporting layer and the like described above. The film forming method of the layers are not particularly limited, and the layers may be produced by any of a dry process and a wet process.

Specific examples of preferred materials that may be used in the organic electroluminescent device are shown below, but the materials that may be used in the invention are not construed as being limited to the example compounds. The compound that is shown as a material having a particular function may also be used as a material having another function. In the structural formulae of the example compounds, R and $R_1$ to $R_{10}$ each independently represent a hydrogen atom or a substituent, and n represents an integer of from 3 to 5.

Preferred examples of a compound that may also be used as the host material of the light-emitting layer are shown below.

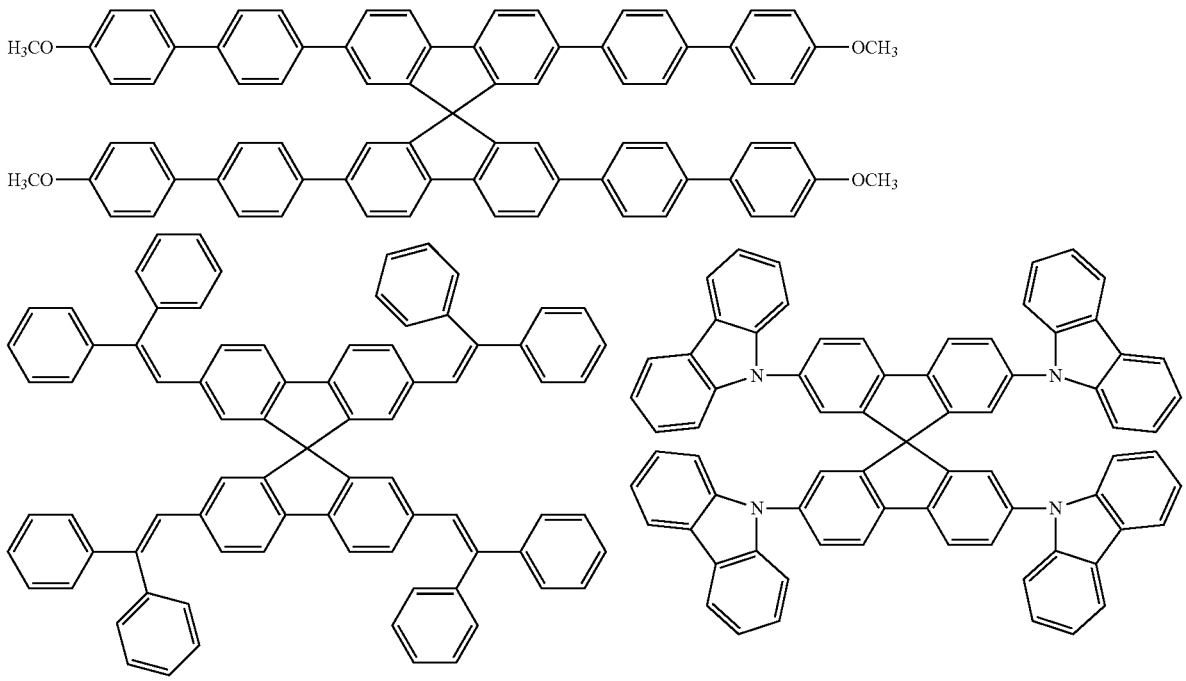

-continued
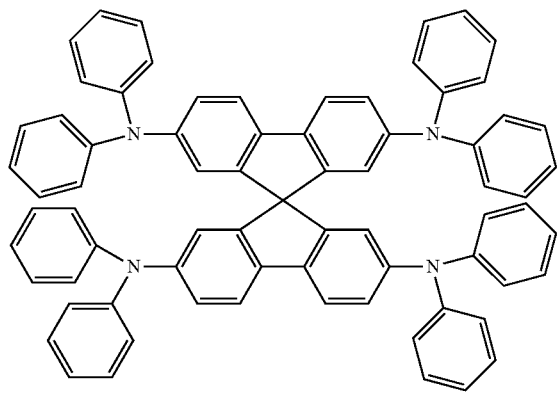
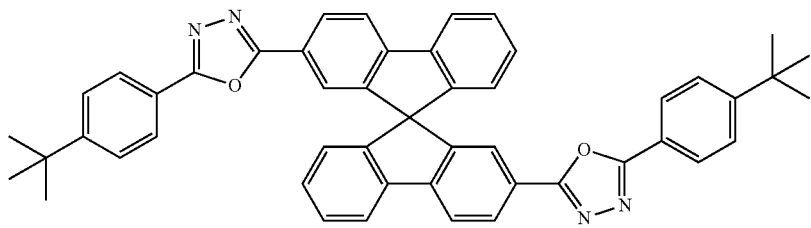
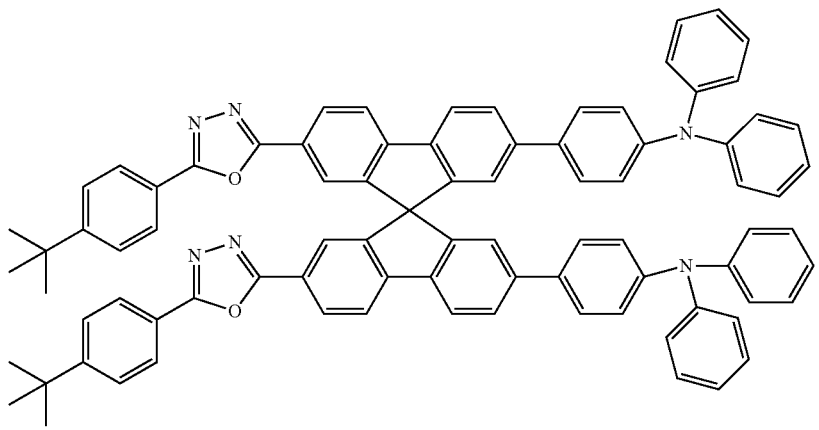
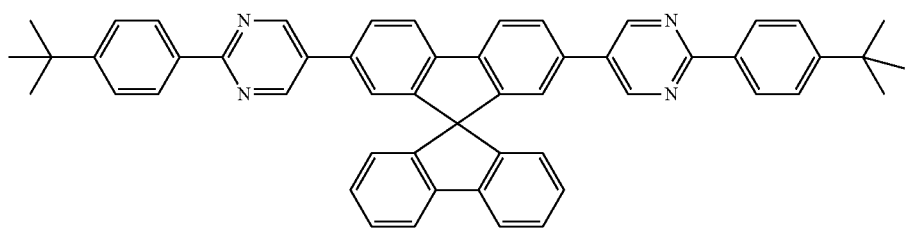
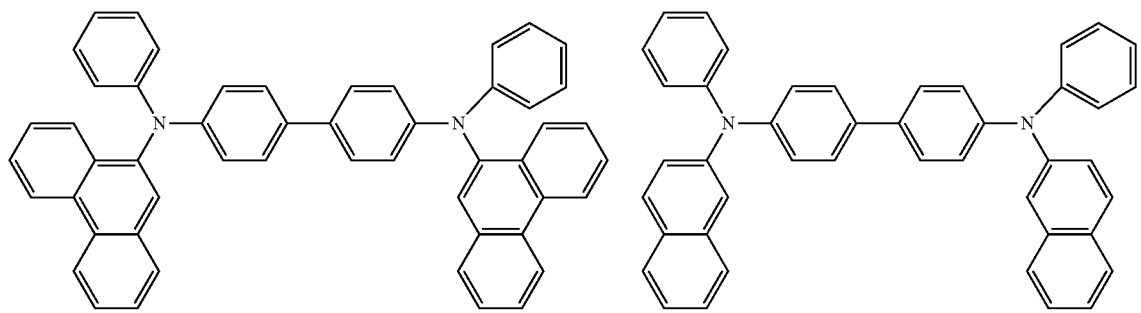

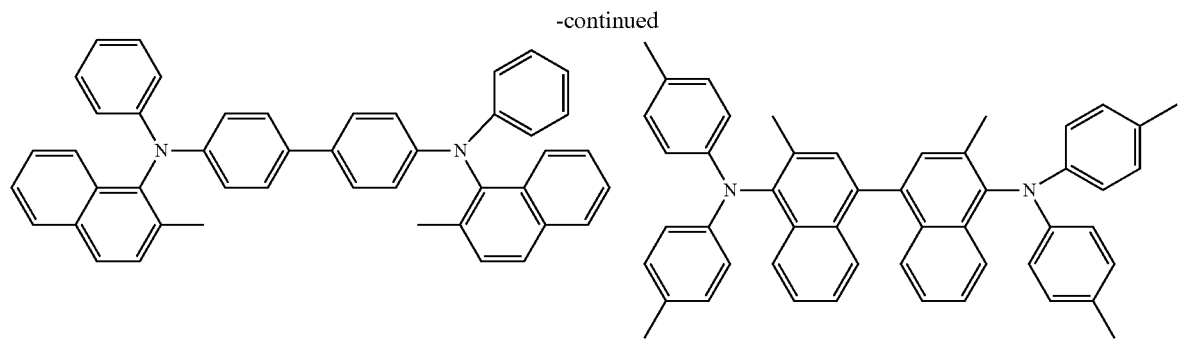
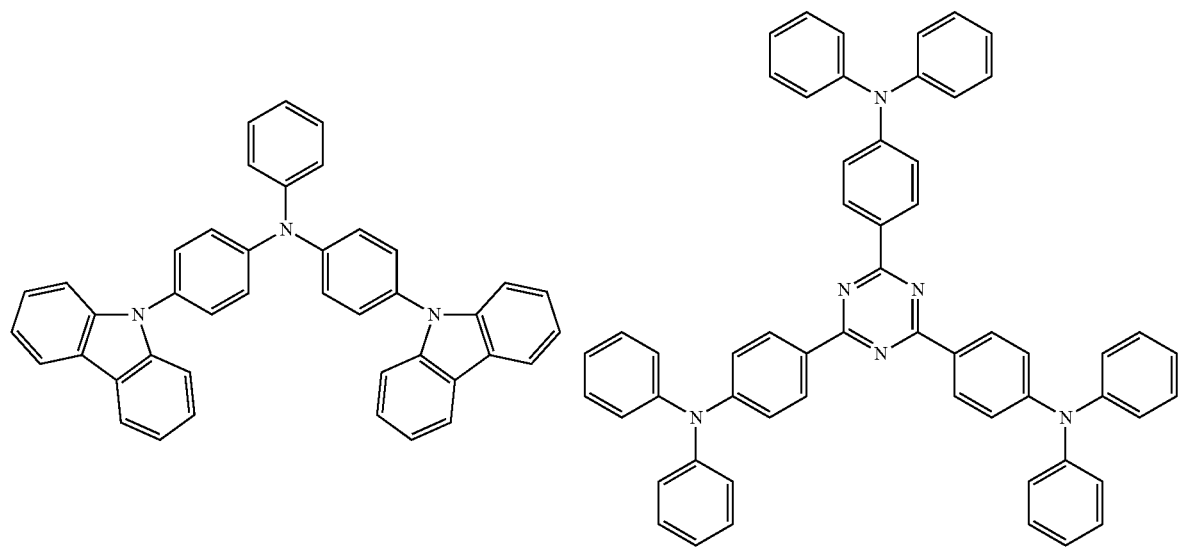
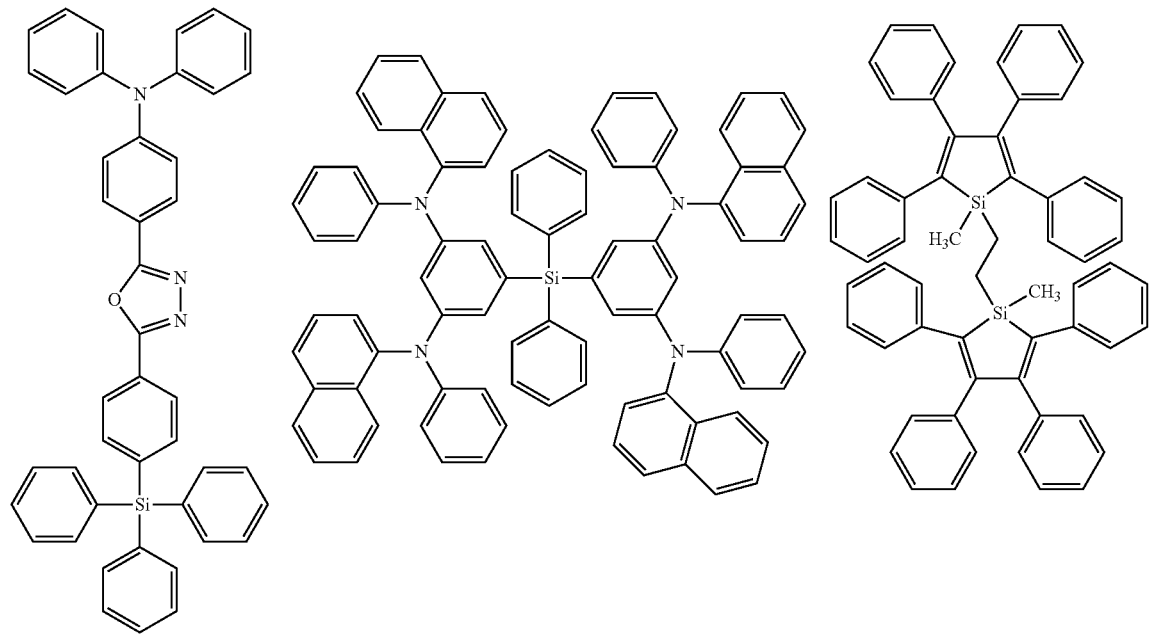

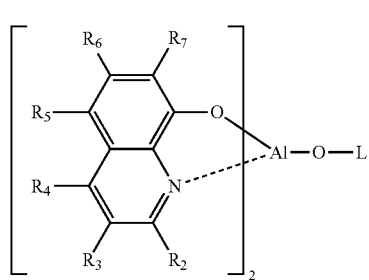
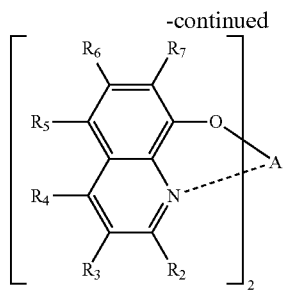
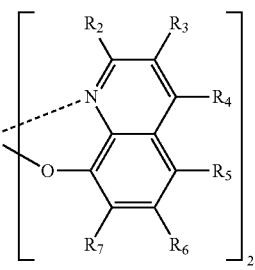
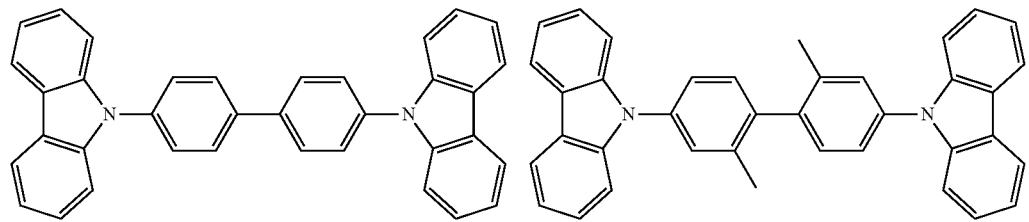
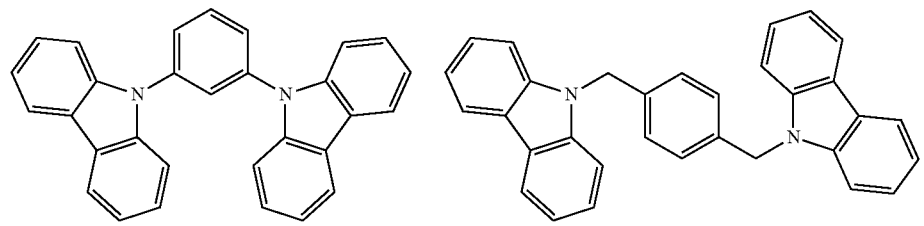
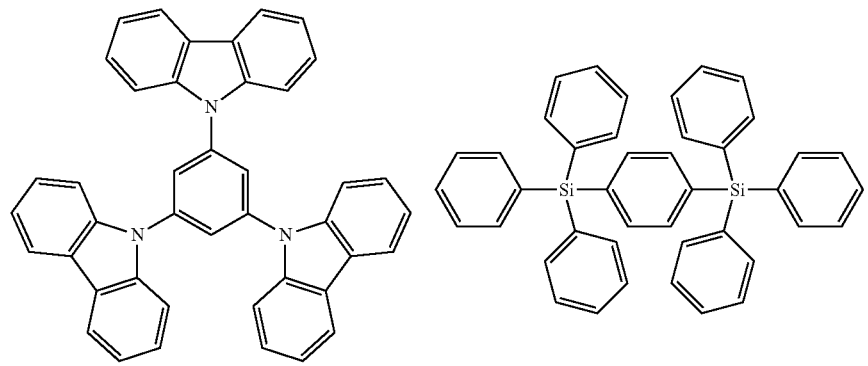
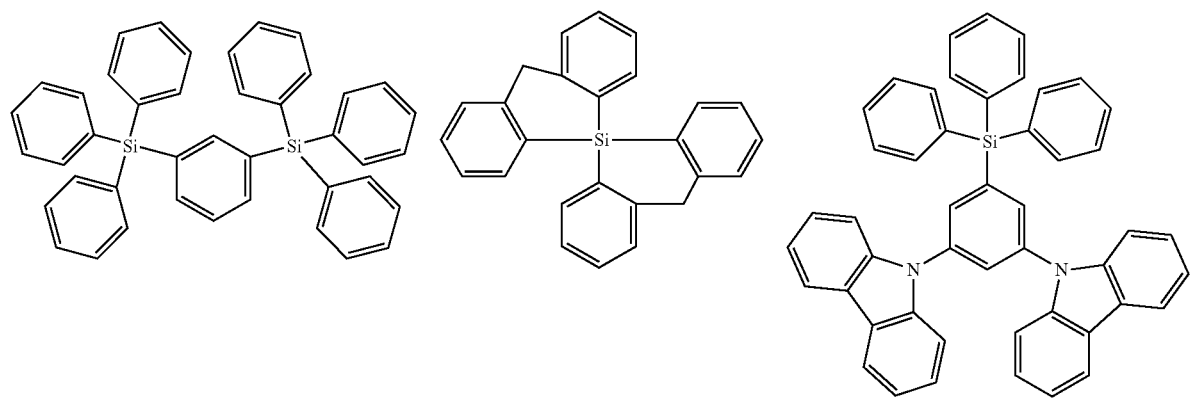

-continued
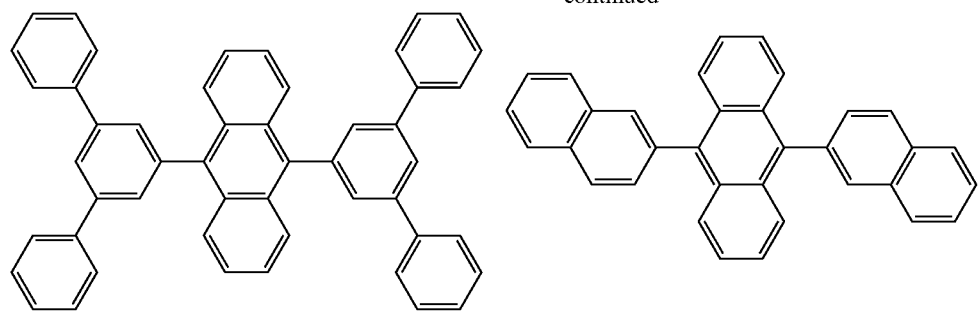
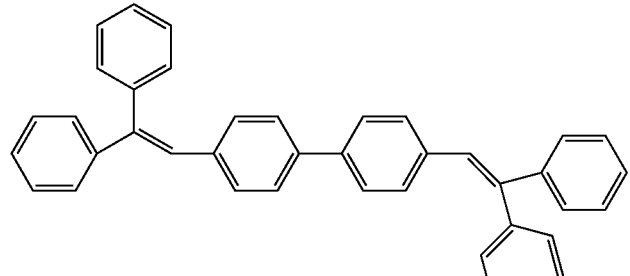
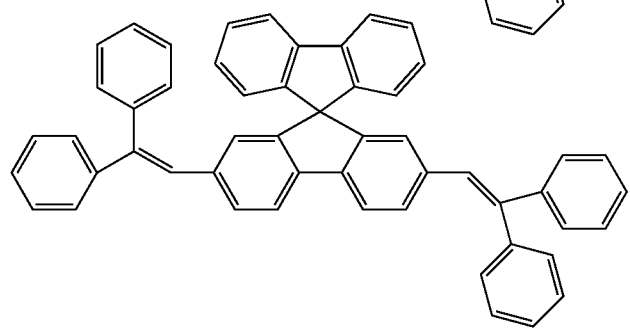
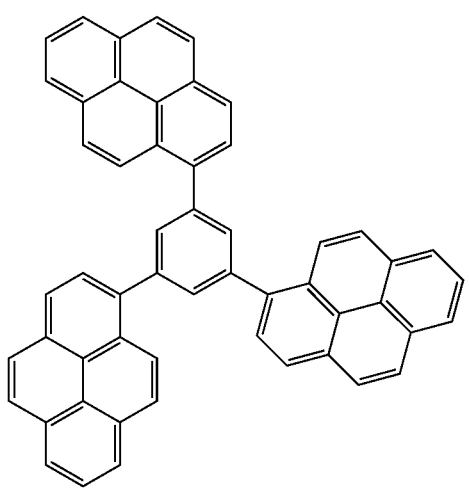
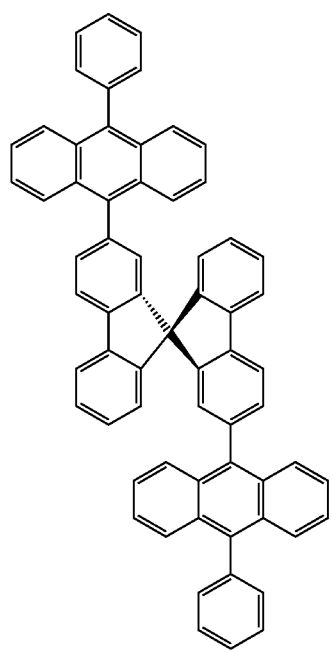
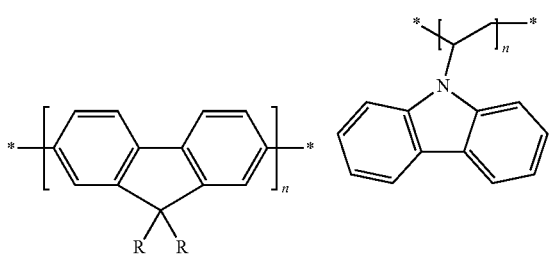

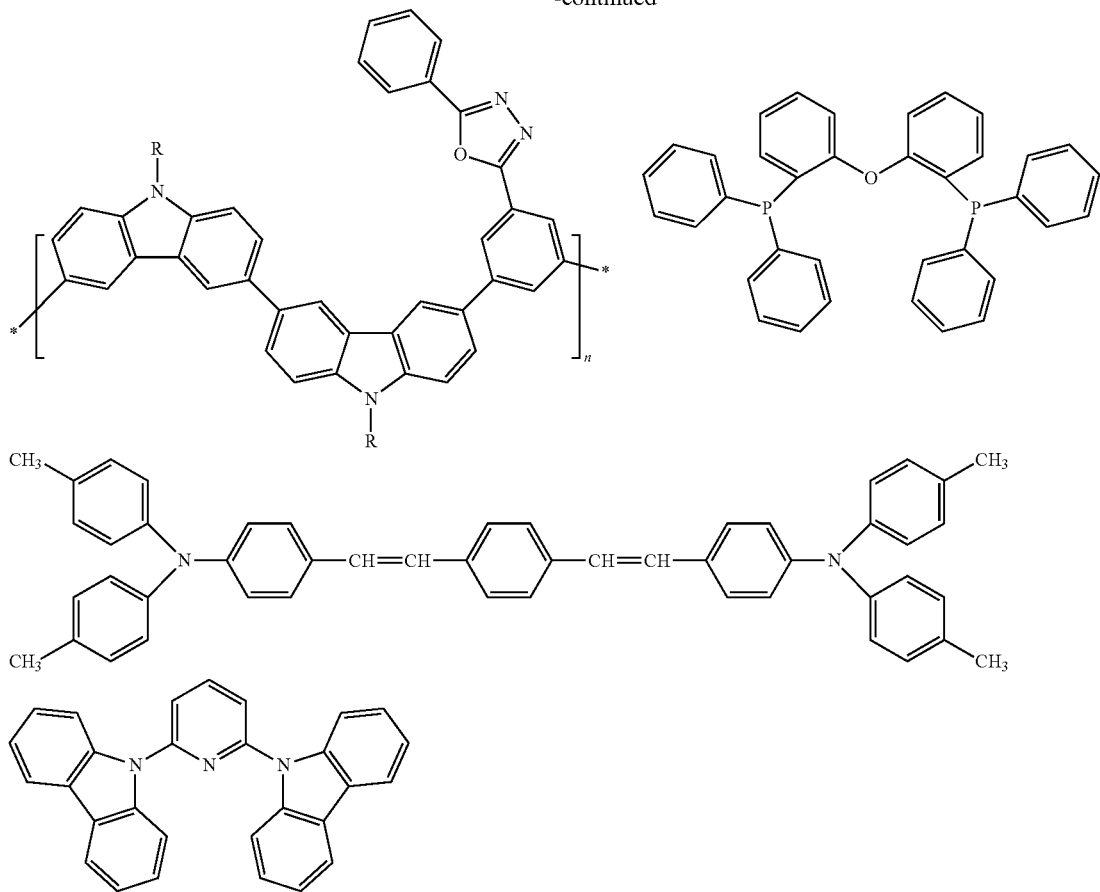
Preferred examples of a compound that may be used as the hole injection material are shown below.
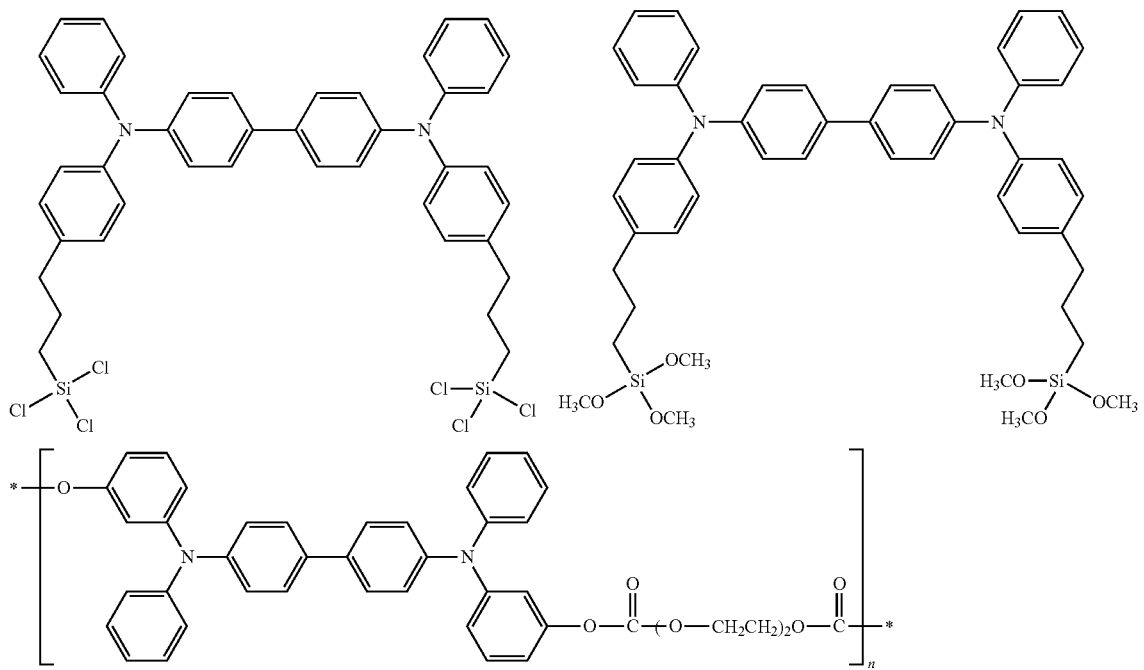

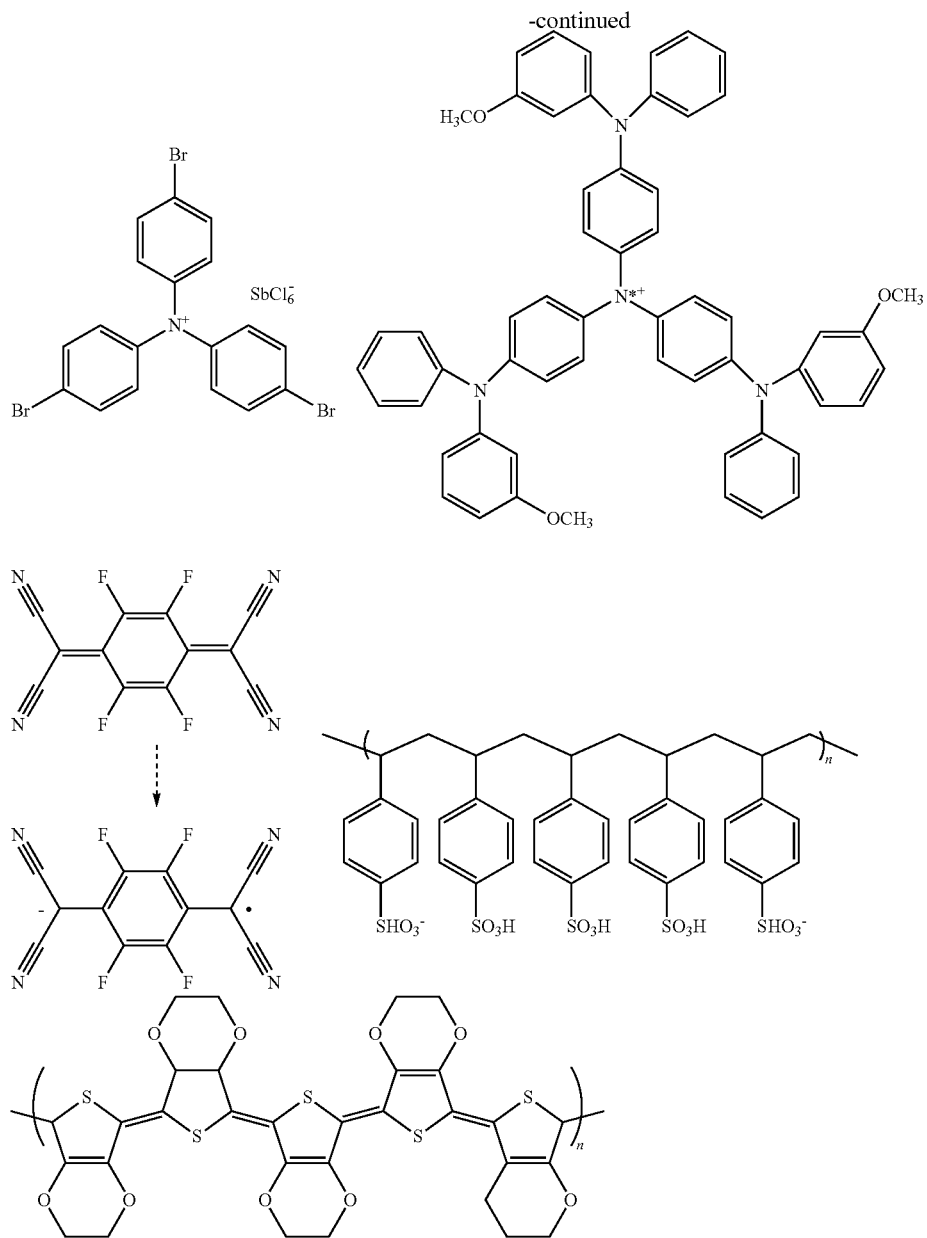
Preferred examples of a compound that may be used as the hole transporting material are shown below.
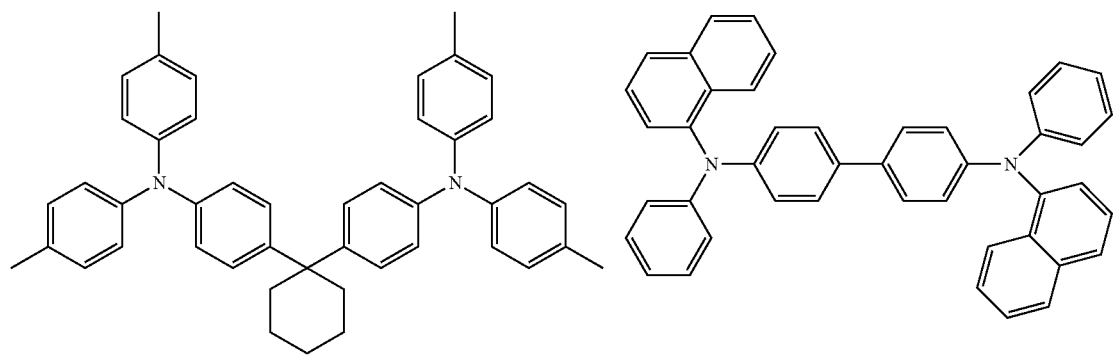

-continued
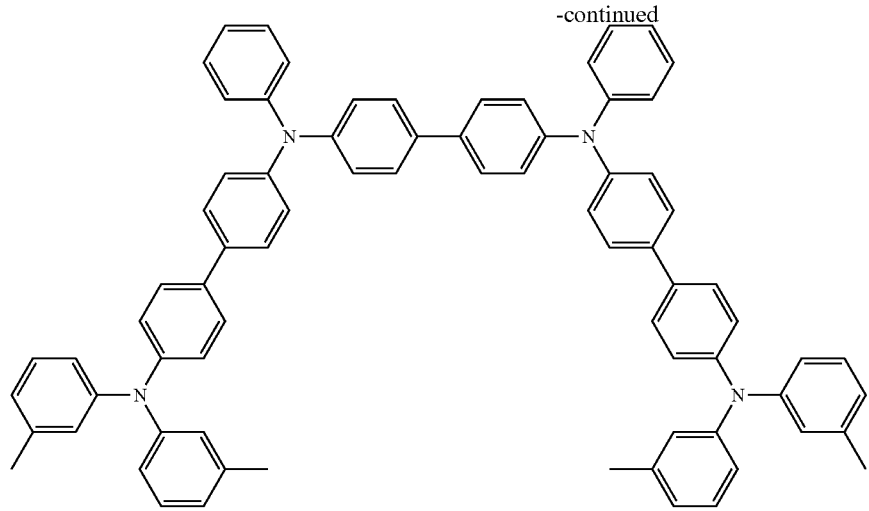
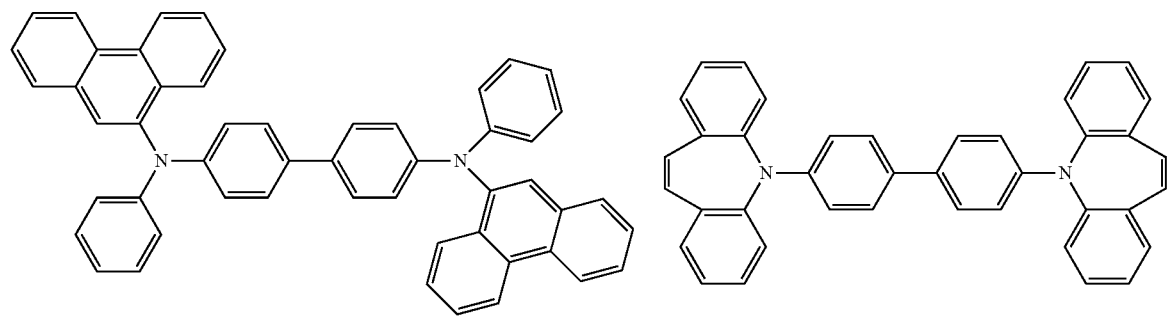
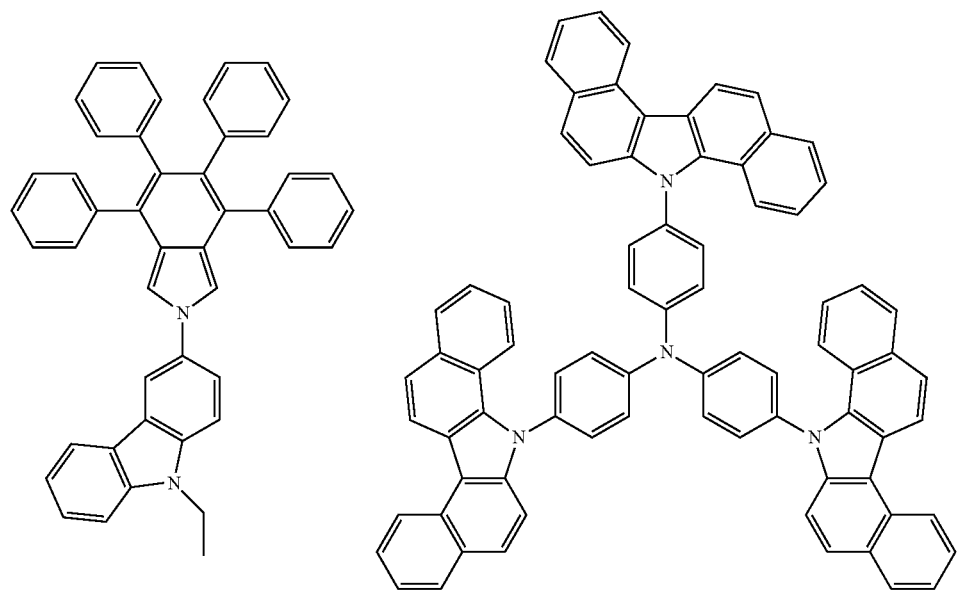

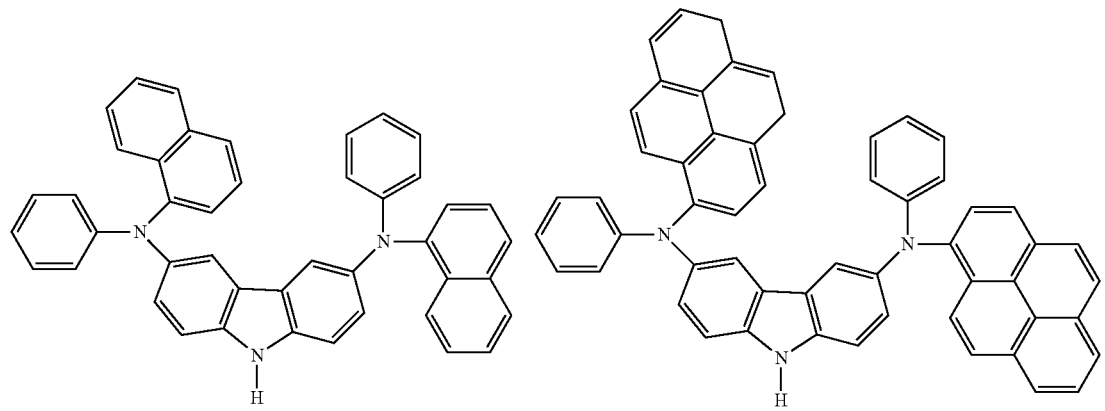
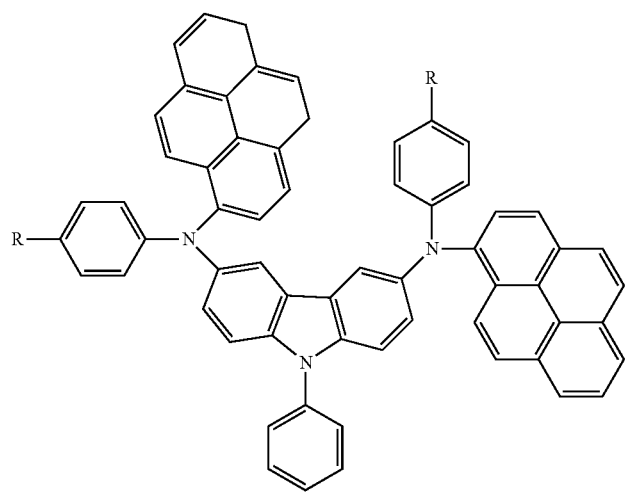
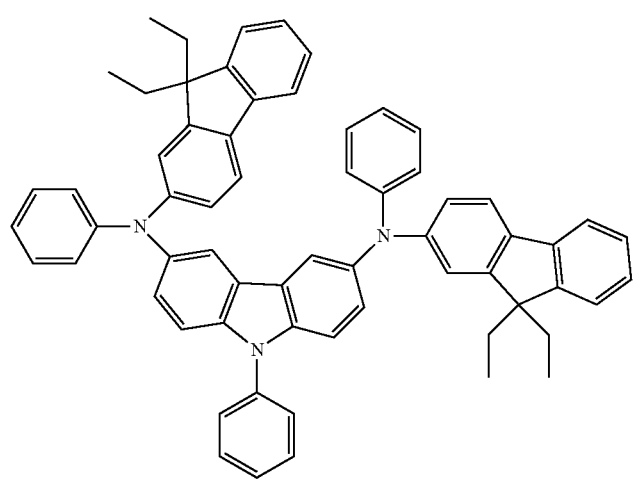

-continued
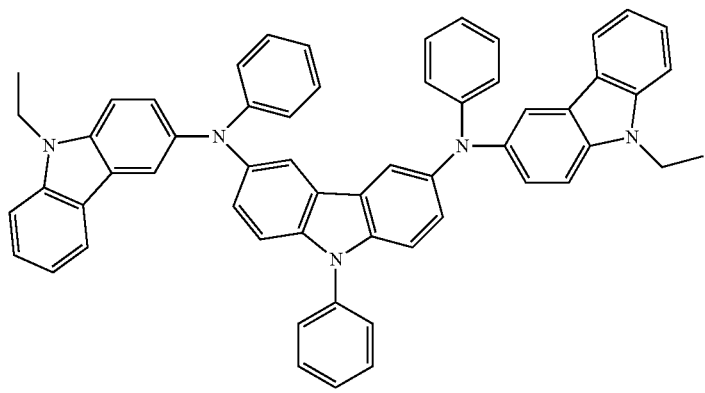
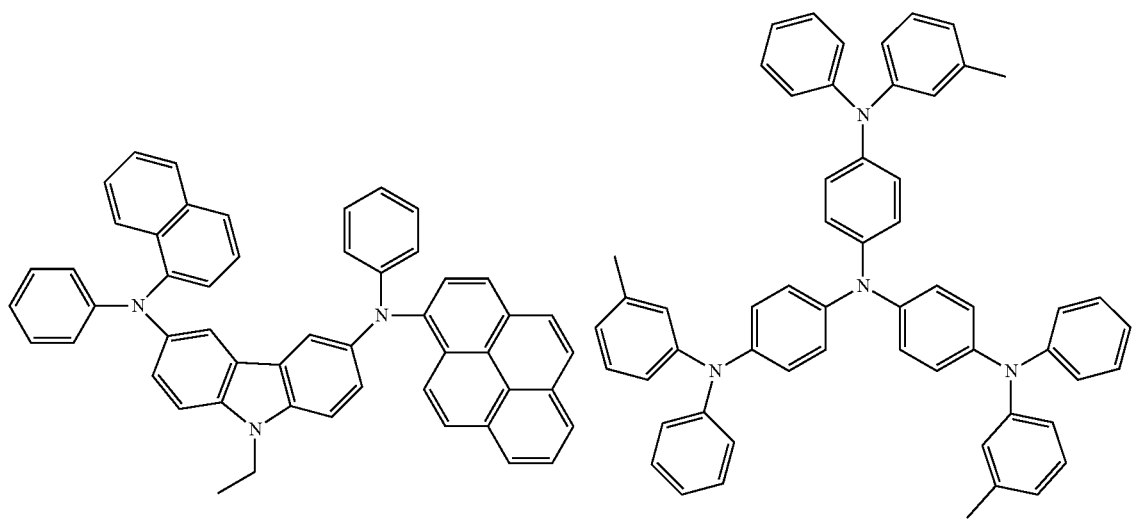
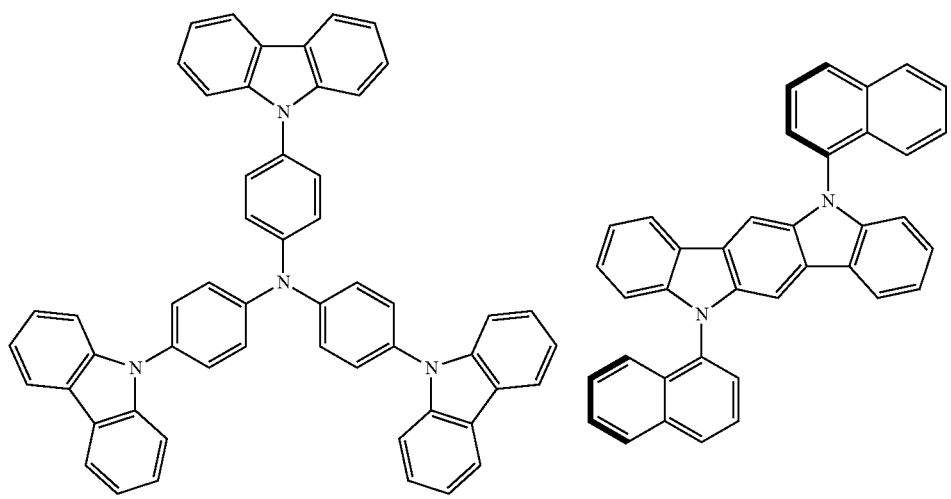

-continued
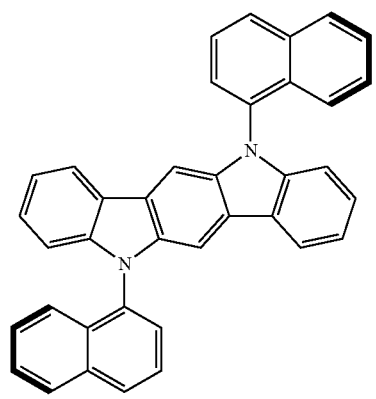 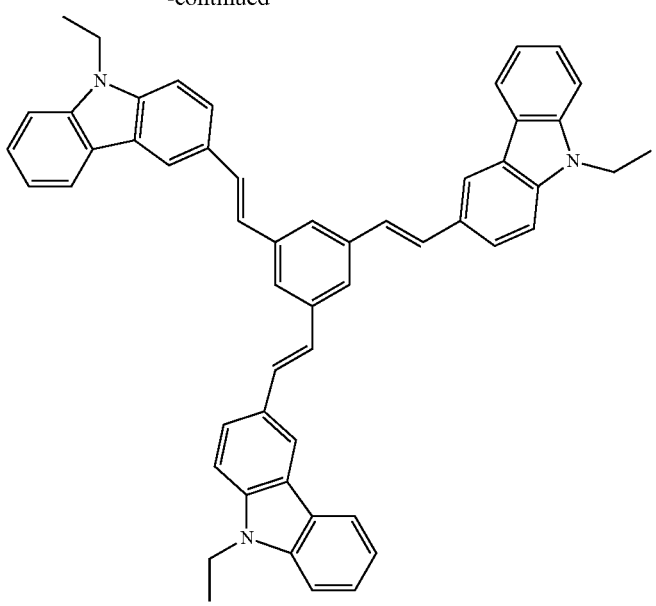
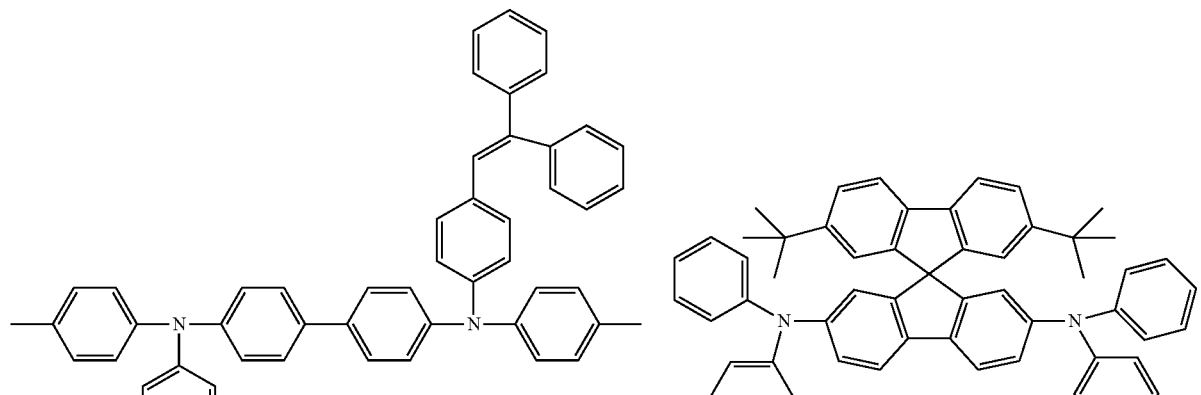
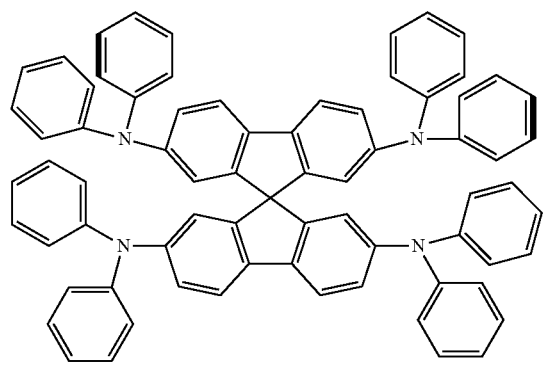 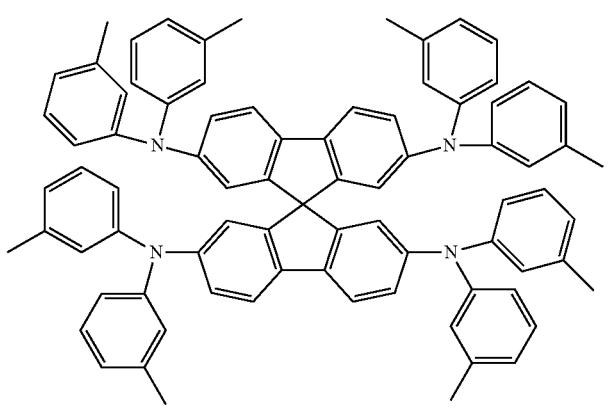

-continued
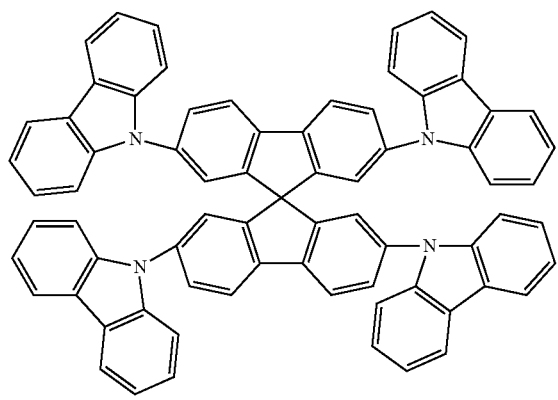
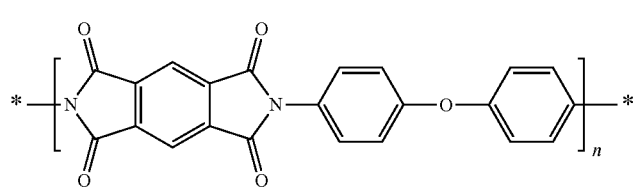
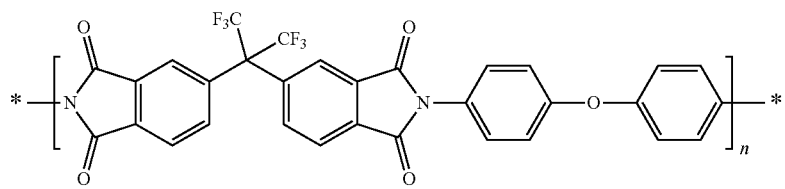
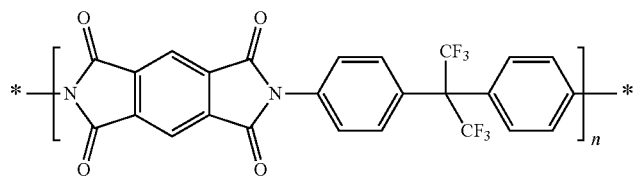
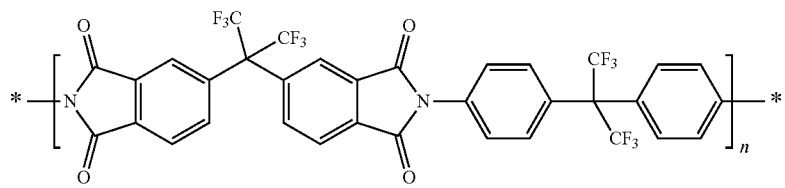
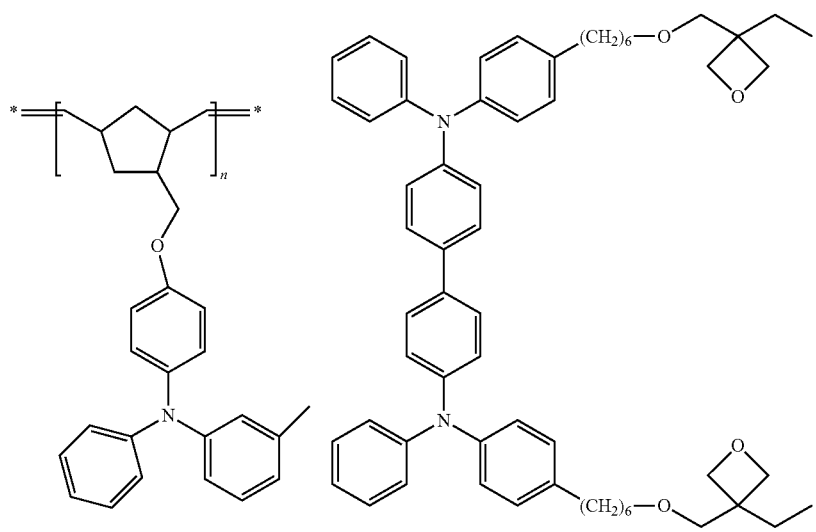

-continued
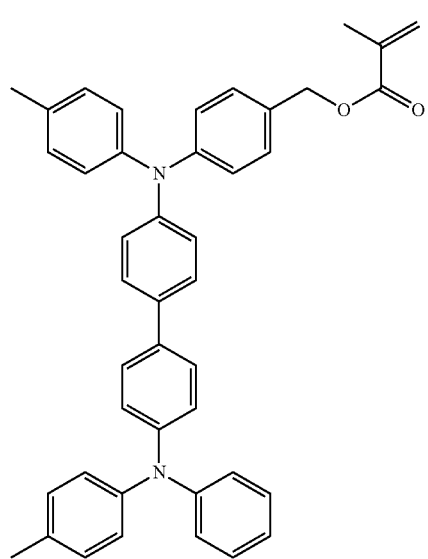
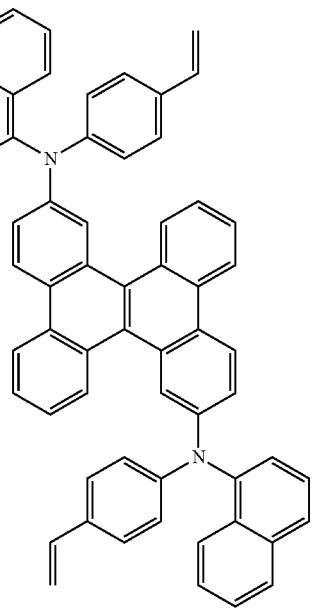
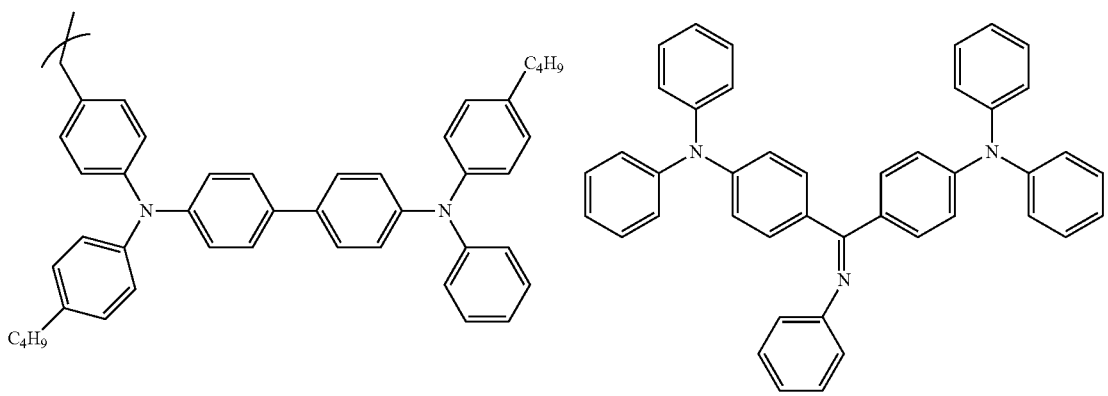
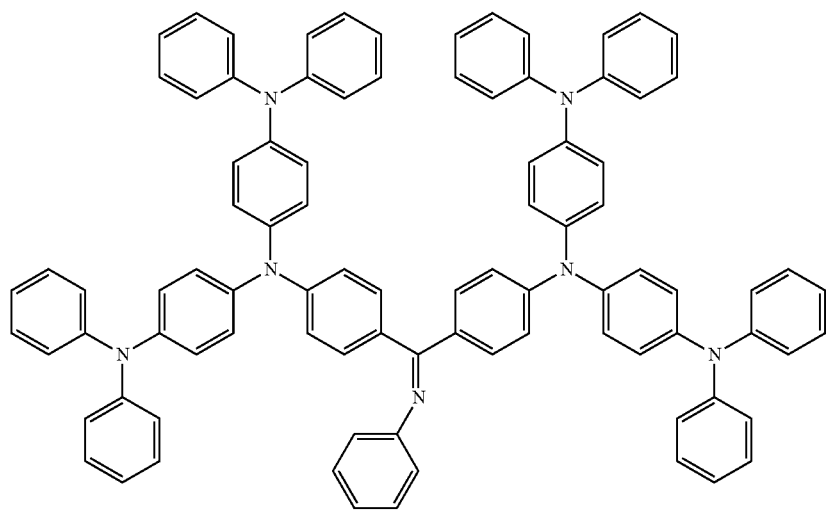

-continued
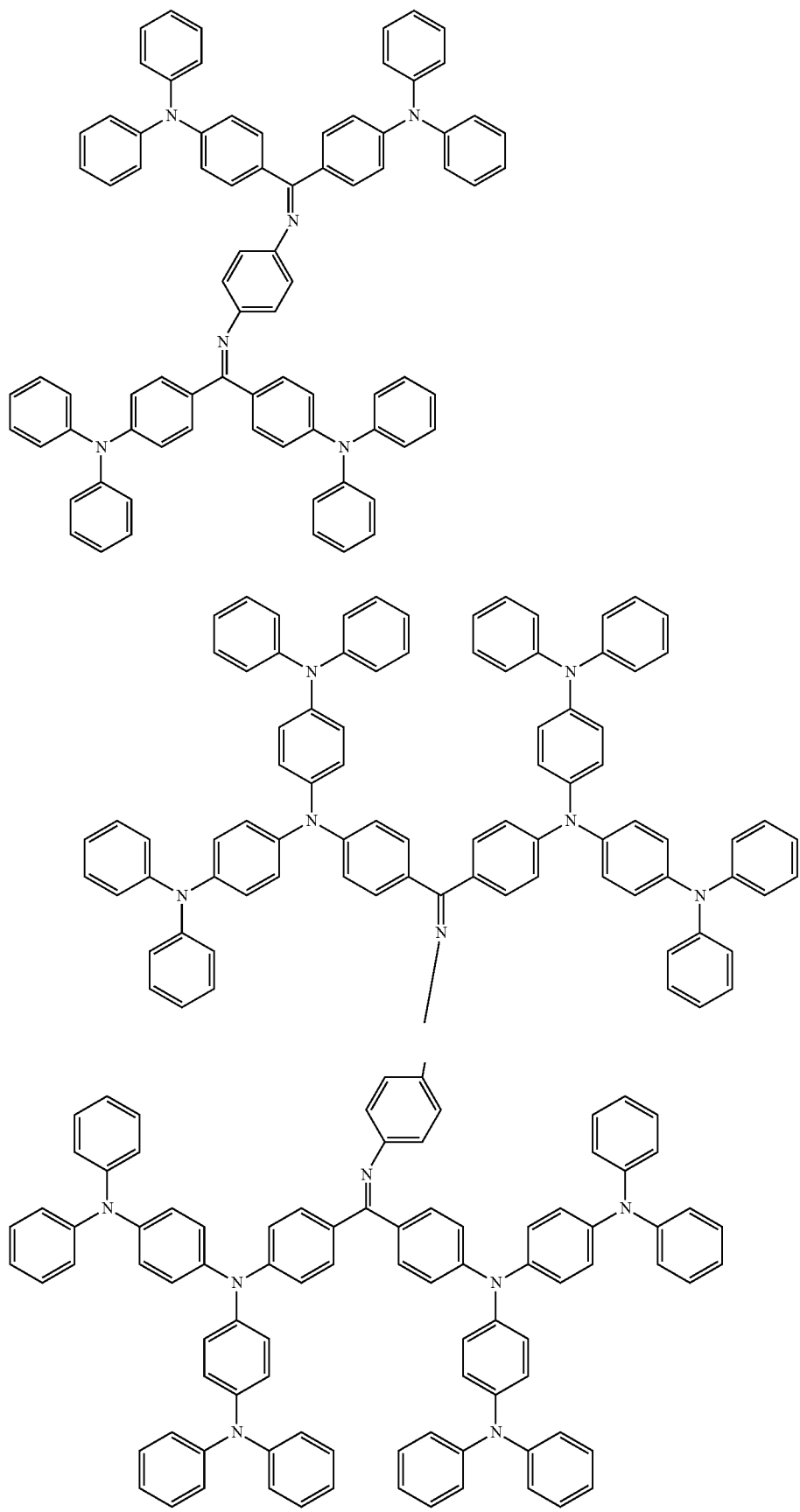

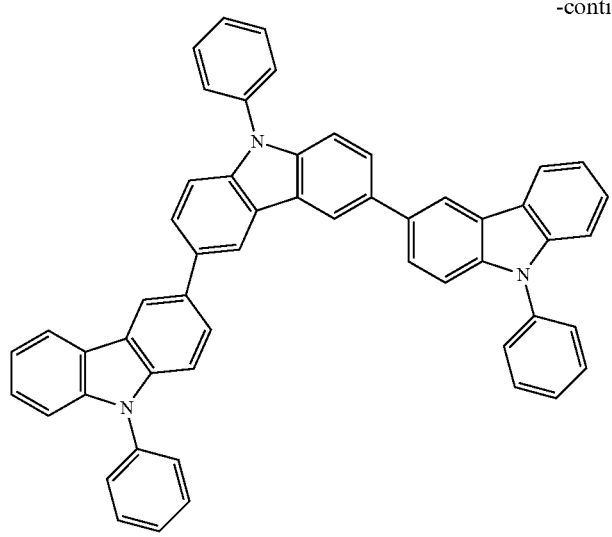
Preferred examples of a compound that may be used as the electron barrier material are shown below.
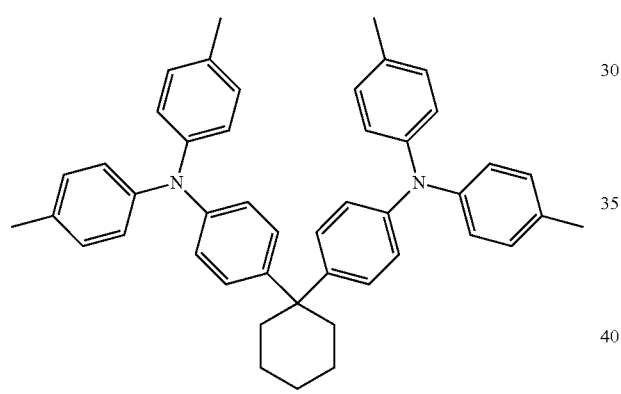
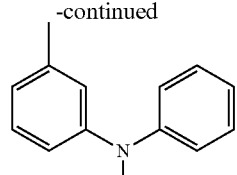
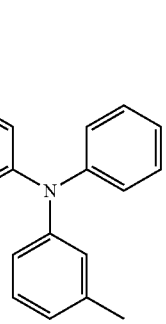
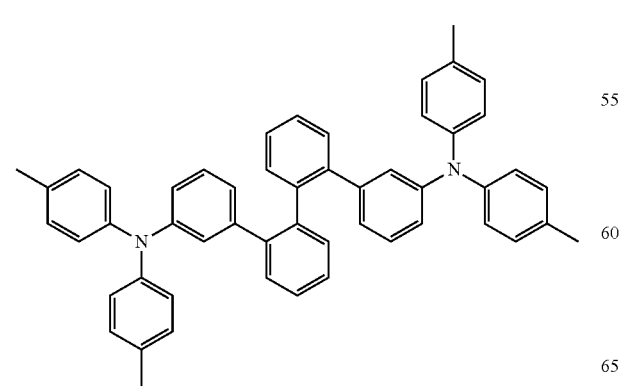
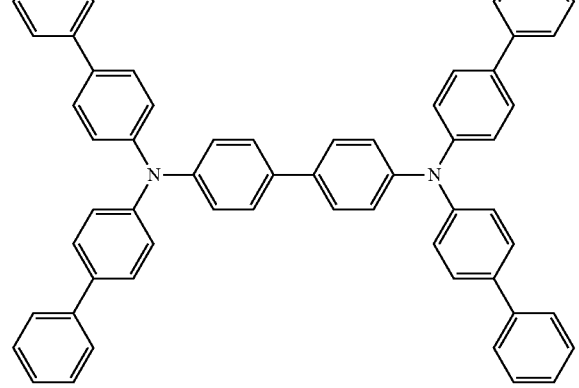
Preferred examples of a compound that may be used as the hole barrier material are shown below.

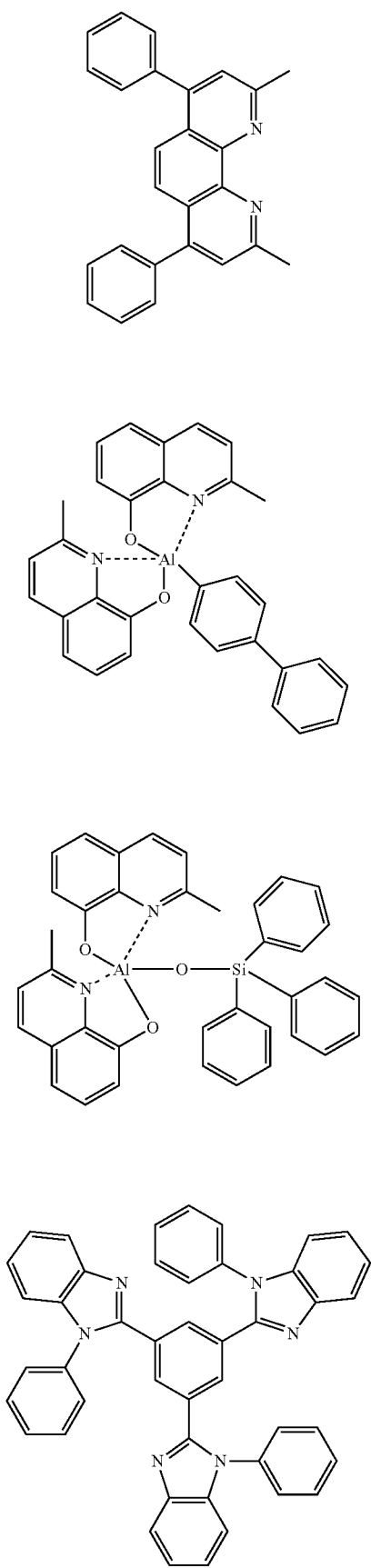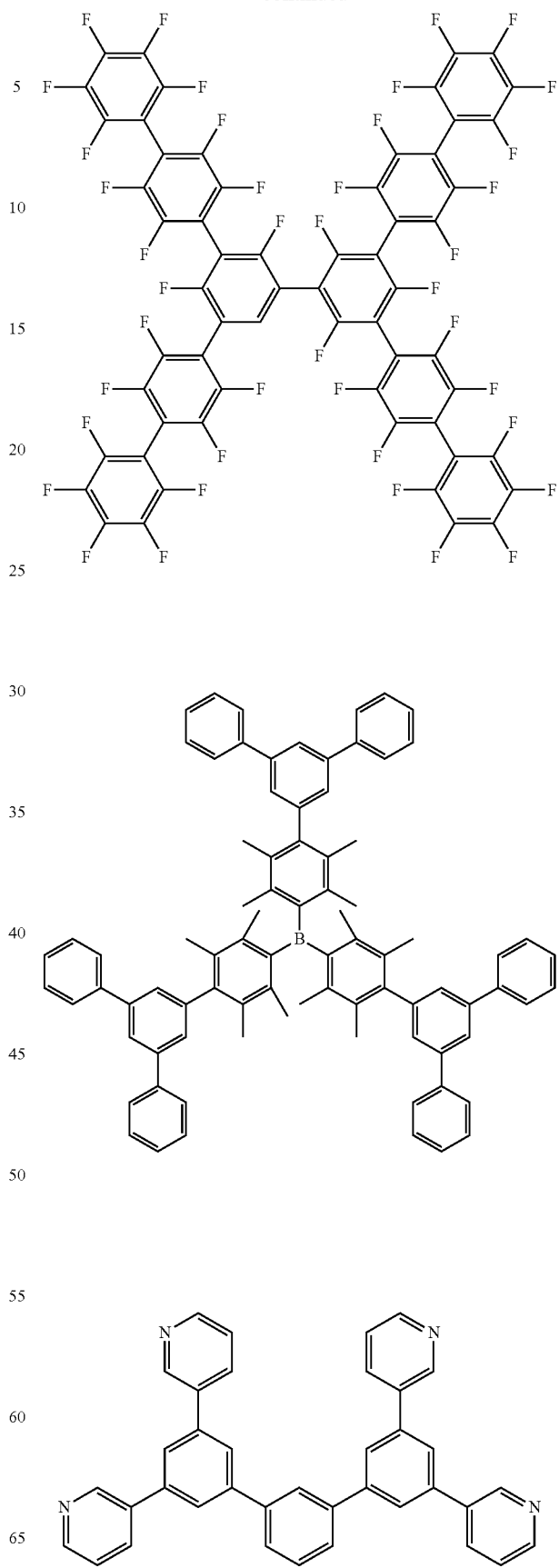

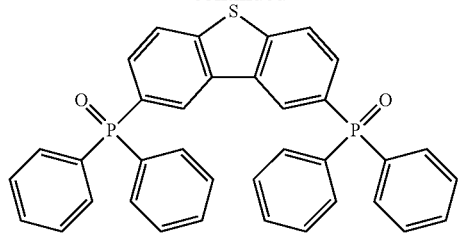
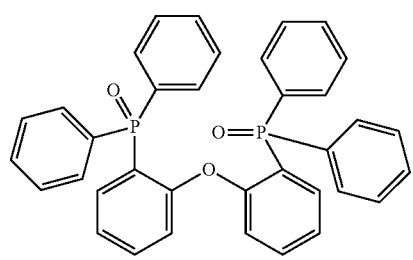
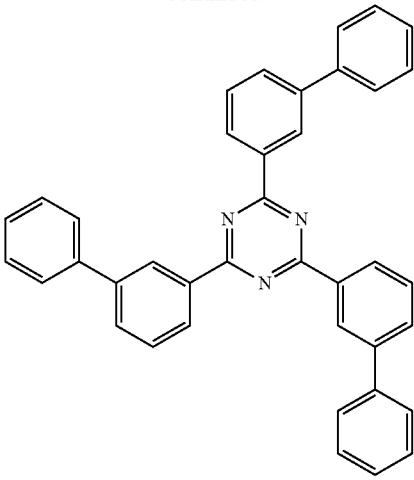
Preferred examples of a compound that may be used as the electron transporting material are shown below.
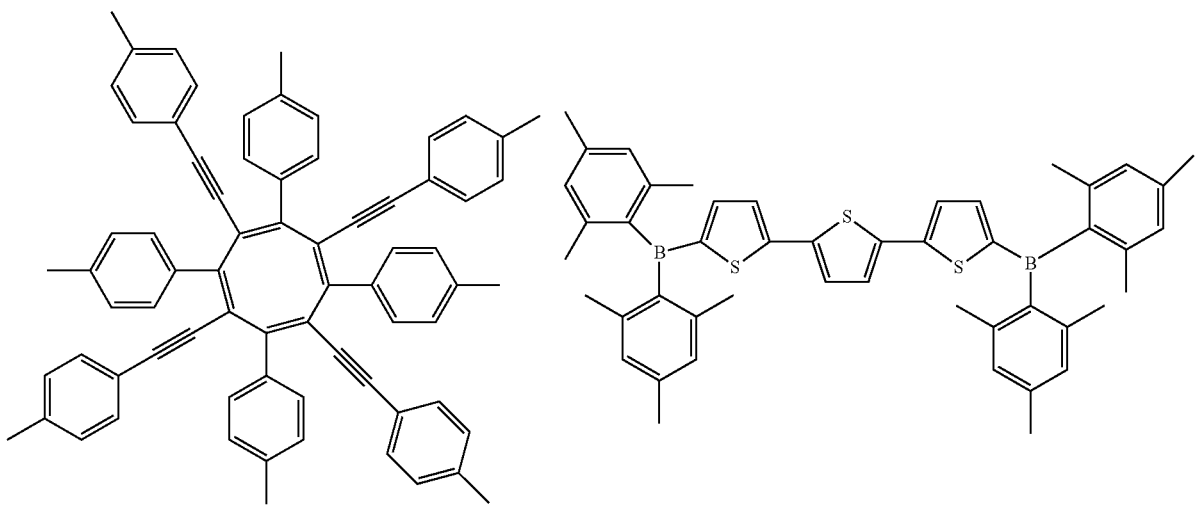
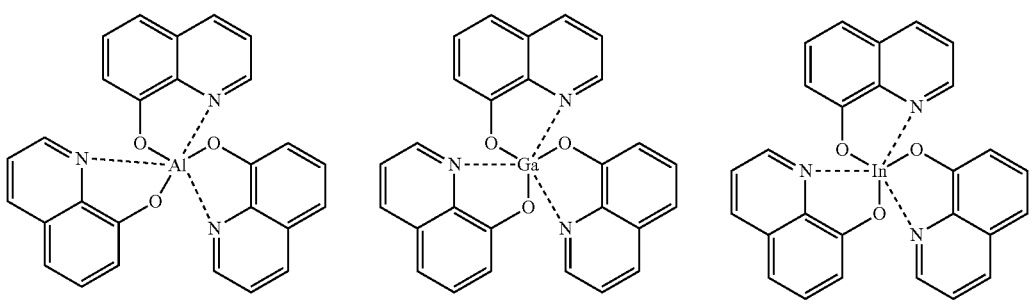

-continued
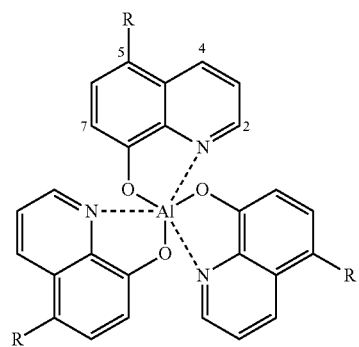
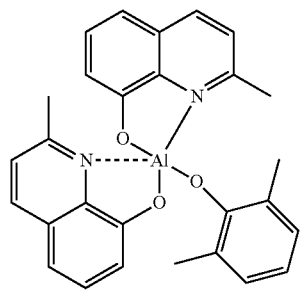
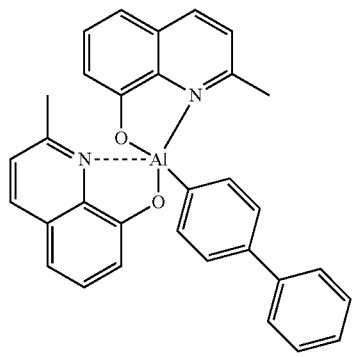
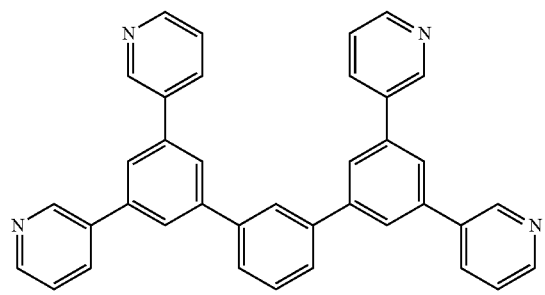
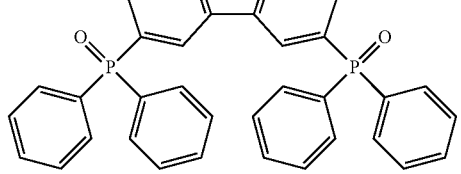
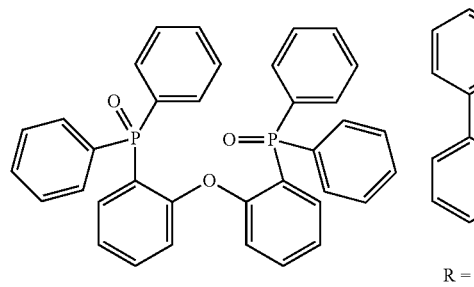
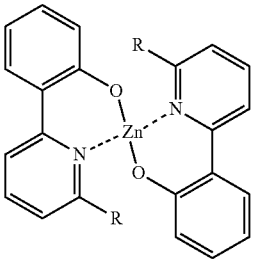
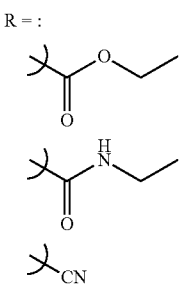
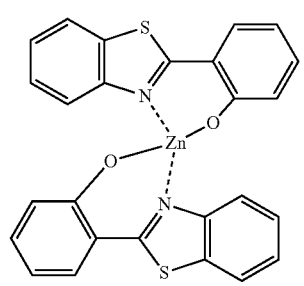
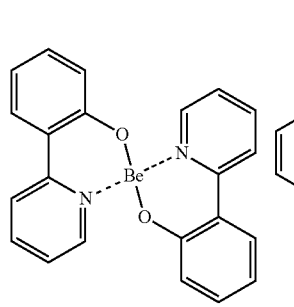
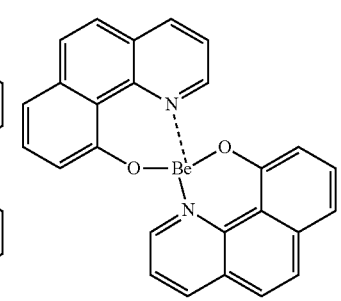
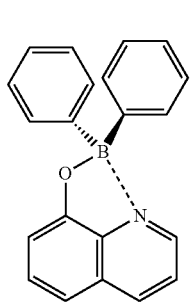
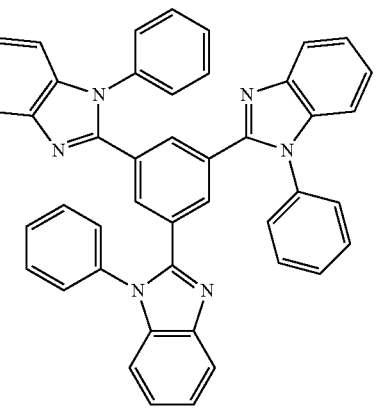

-continued
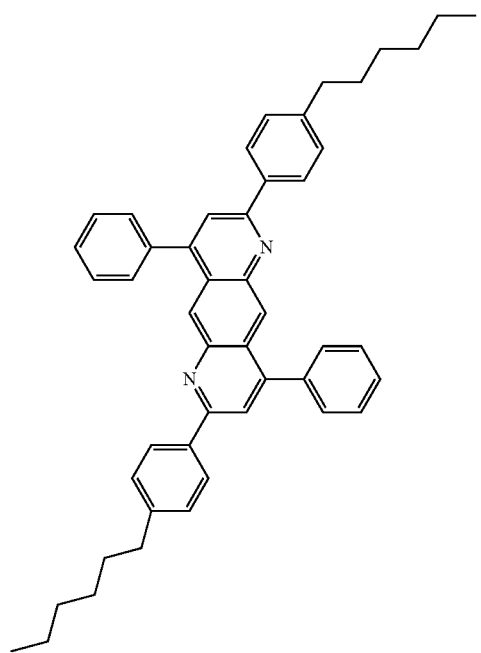
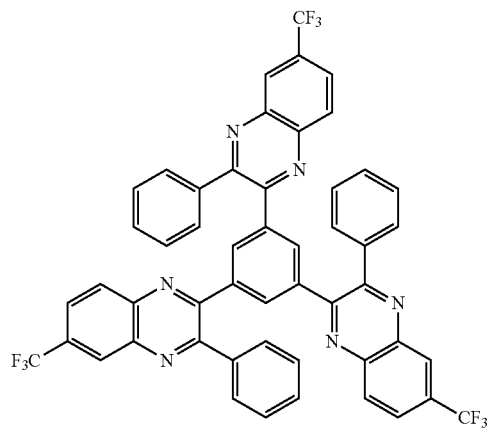
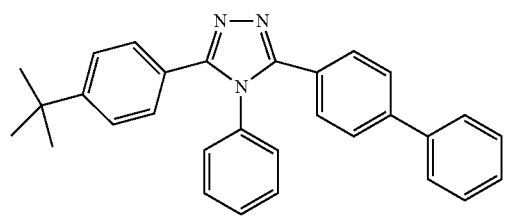
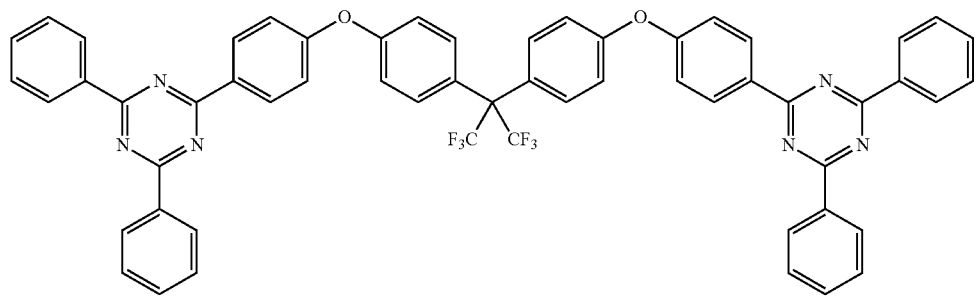
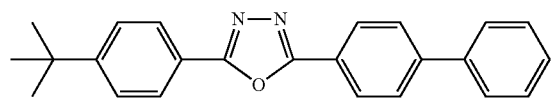
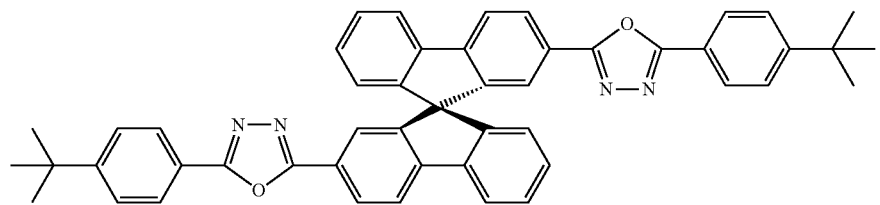

-continued
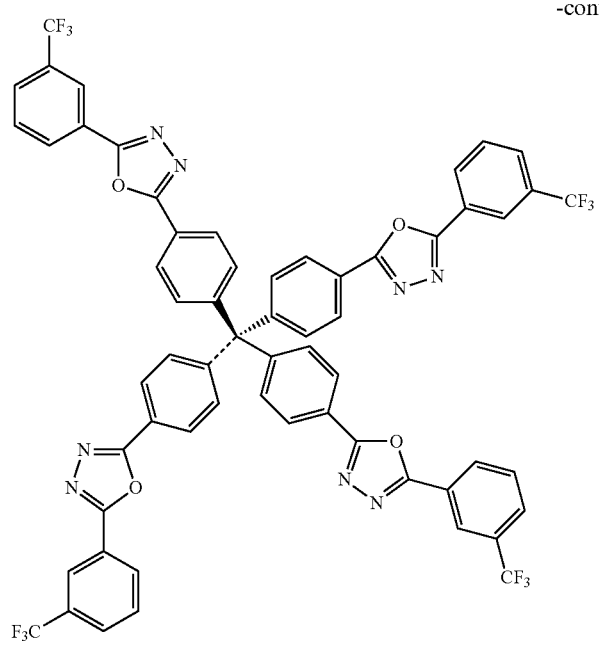
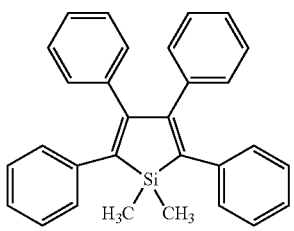
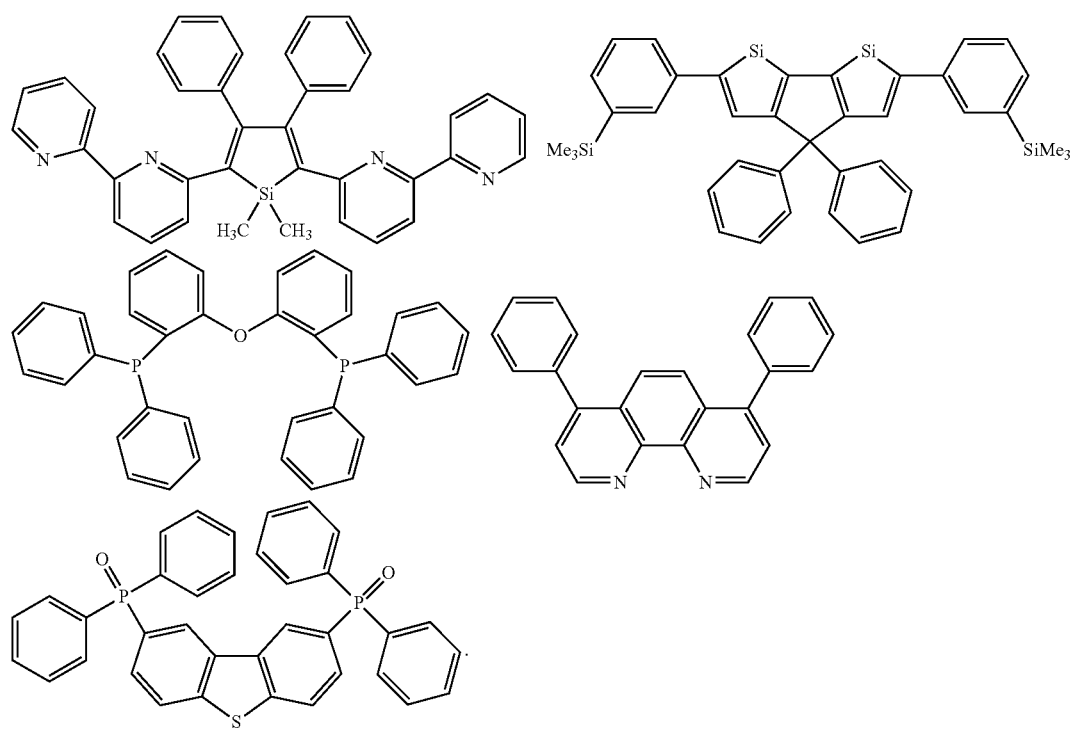
Preferred examples of a compound that may be used as the electron injection material are shown below.
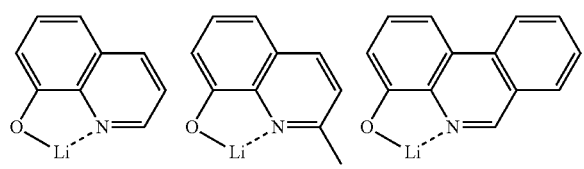
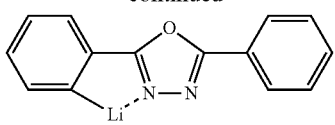
Preferred examples of a compound as a material that may be added are shown below. For example, the compound may be added as a stabilizing material.

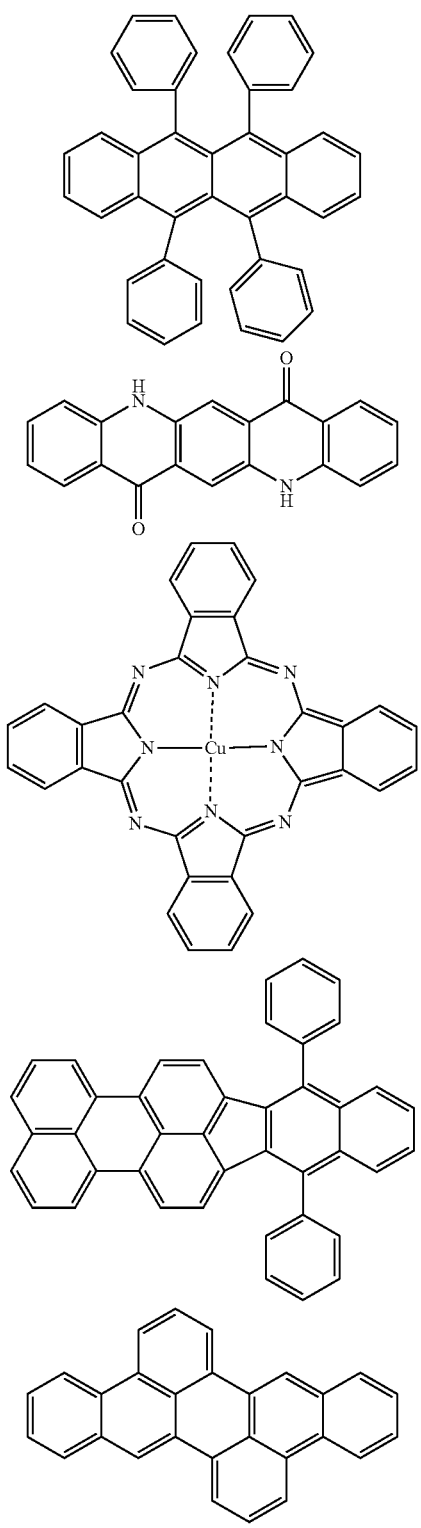

The organic electroluminescent device thus produced by the aforementioned method emits light on application of an electric field between the anode and the cathode of the obtained device. In this case, when the light emission is caused by the excited singlet energy, light having a wavelength that corresponds to the energy level thereof may be confirmed as fluorescent light and delayed fluorescent light.

When the light emission is caused by the excited triplet energy, light having a wavelength that corresponds to the energy level thereof may be confirmed as phosphorescent light. The normal fluorescent light has a shorter light emission lifetime than the delayed fluorescent light, and thus the light emission lifetime may be distinguished between the fluorescent light and the delayed fluorescent light.

The phosphorescent light may substantially not observed with a normal organic compound, such as the compound of the invention, at room temperature since the excited triplet energy is converted to heat or the like due to the instability thereof, and is immediately deactivated with a short lifetime. The excited triplet energy of the normal organic compound may be measured by observing light emission under an extremely low temperature condition.

The organic electroluminescent device of the invention may be applied to any of a single device, a structure with plural devices disposed in an array, and a structure having anodes and cathodes disposed in an X-Y matrix. According to the invention, an organic light-emitting device that is largely improved in light emission efficiency may be obtained by adding the compound represented by the general formula (1) in the light-emitting layer. The organic light-emitting device, such as the organic electroluminescent device, of the invention may be applied to a further wide range of purposes. For example, an organic electroluminescent display apparatus may be produced with the organic electroluminescent device of the invention, and for the details thereof, reference may be made to S. Tokito, C. Adachi and H. Murata, "Yuki EL Display" (Organic EL Display) (Ohmsha, Ltd.). In particular, the organic electroluminescent device of the invention may be applied to organic electroluminescent illumination and backlight which are highly demanded.

EXAMPLE

The features of the invention will be described more specifically with reference to synthesis examples and working examples below. The materials, processes, procedures and the like shown below may be appropriately modified unless they deviate from the substance of the invention. Accordingly, the scope of the invention is not construed as being limited to the specific examples shown below.

Synthesis Example 1

Synthesis of Compound 1

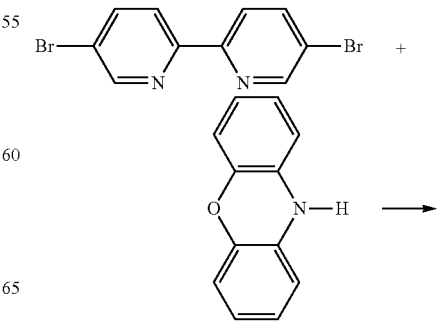

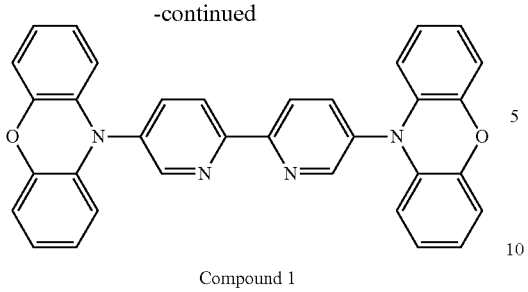

Compound 1

4,4'-Dibromobipyridine (3.14 g, 10 mmol), phenoxazine (4.40 g, 24 mmol), bis(dibenzylideneacetone) palladium (Pd(dba)$_2$, 0.46 g, 0.8 mmol), sodium tert-butoxide (NaOt-Bt, 2.88 g, 30 mmol), and tri(tert-butyl)phosphonium tetrafluoroborate (tBu$_3$P.HBF$_4$, 0.116 g, 0.4 mmol) were added to 50 mL of dehydrated toluene, and heated for 24 hours while maintaining the inner temperature to 100° C. After the reaction liquid was allowed to cool, 200 mL of water was added thereto, and the mixture was separated. The organic layer was concentrated, and the concentrate was purified by SiO$_2$ column chromatography with a mixed solvent of chloroform and hexane (1/1) as a developing solvent. According to the procedures, the compound 1 was obtained at a yield amount of 3.10 g and a yield of 60%. The purified product of the compound 1 was further subjected to sublimation purification under condition of 320° C. and 1 Pa or less.

$^1$H NMR (600 MHz, CDCl$_3$) δ 8.9-8.5 (2H), 7.8-7.5 (2H), 7.4-6.8 (18H); MS (70 eV, EI) m/z=518 (M+)

Synthesis Example 2

Synthesis of Compound 2

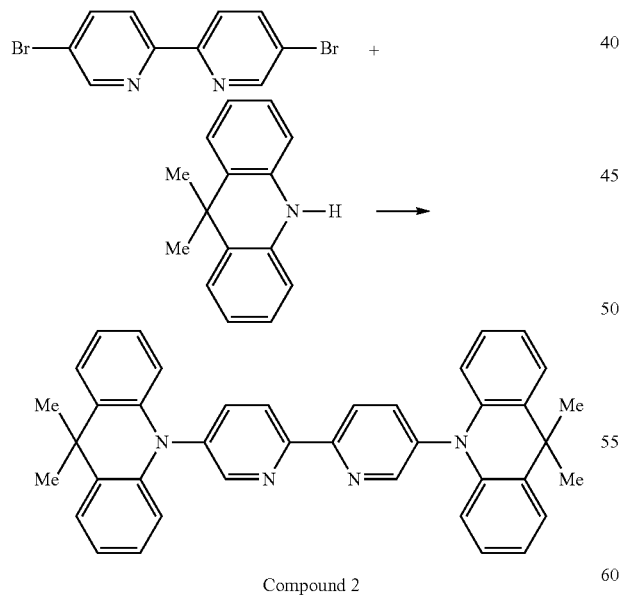

Compound 2

The synthesis process and the purification by column chromatography were performed in the same manner as in Synthesis Example 1 except that dimethylacridan (5.02 g, 24 mmol) was used instead of phenoxazine (4.40 g, 24 mmol), and thus the compound 2 was obtained at a yield amount of 2.28 g and a yield of 40%. Thereafter, the purified product of the compound 2 was subjected to sublimation purification under condition of 320° C. and 1 Pa or less.

$^1$H NMR (600 MHz, CDCl$_3$) δ 8.9-8.6 (2H), 7.9-7.5 (2H), 7.4-6.5 (18H), 1.5-1.9 (12H); MS (70 eV, EI) m/z=570 (M+), 555 (M$^+$-15)

Synthesis Example 3

Synthesis of Compound 3

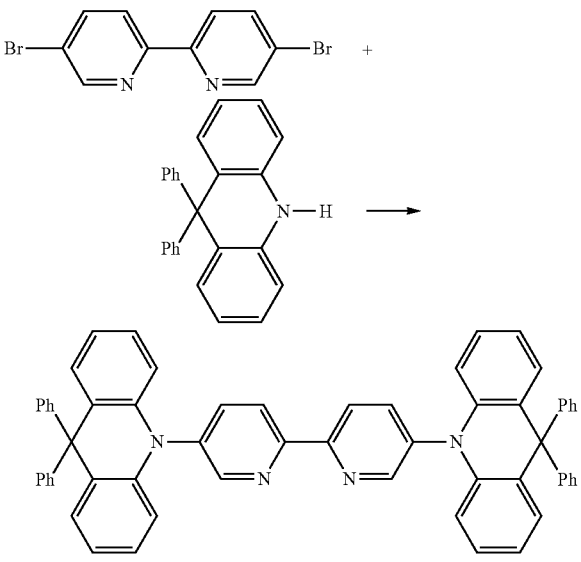

Compound 3

The synthesis process and the purification by column chromatography were performed in the same manner as in Synthesis Example 1 except that 4,4'-dibromobipyridine (1.57 g, 5 mmol) and diphenylacridan (4.00 g, 12 mmol) were used instead of 4,4'-dibromobipyridine (3.14 g, 10 mmol) and phenoxazine (4.40 g, 24 mmol), and thus the compound 3 was obtained at a yield amount of 2.25 g and a yield of 55%. Thereafter, the purified product of the compound 3 was subjected to sublimation purification under condition of 320° C. and 1 Pa or less.

$^1$H NMR (600 MHz, CDCl$_3$) δ 8.9-8.6 (2H), 7.9-7.5 (2H), 7.4-6.5 (38H); MS (70 eV, EI) m/z=819 (M+)

Synthesis Example 4

Synthesis of Compound 4

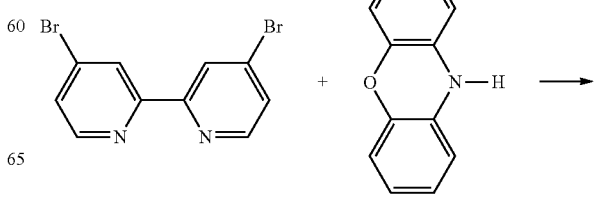

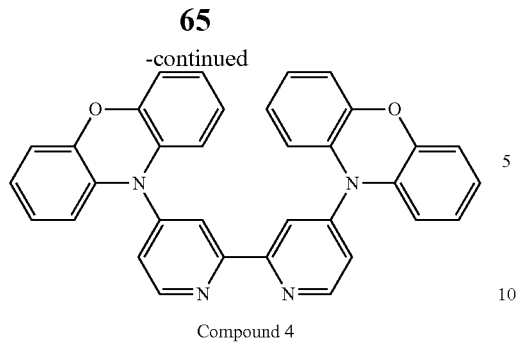

Compound 4

The synthesis process and the purification by column chromatography were performed in the same manner as in Synthesis Example 1 except that 5,5'-dibromobipyridine (3.14 g, 10 mmol) was used instead of 4,4'-dibromobipyridine (3.14 g, 10 mmol), and thus the compound 4 was obtained at a yield amount of 2.33 g and a yield of 45%. Thereafter, the purified product of the compound 4 was subjected to sublimation purification under condition of 320° C. and 1 Pa or less.

$^1$H NMR (600 MHz, CDCl$_3$) δ 8.6-8.1 (2H), 8.0-7.6 (2H), 7.4-6.5 (18H); MS (70 eV, EI) m/z=518 (M+)

Synthesis Example 5

Synthesis of Compound 5

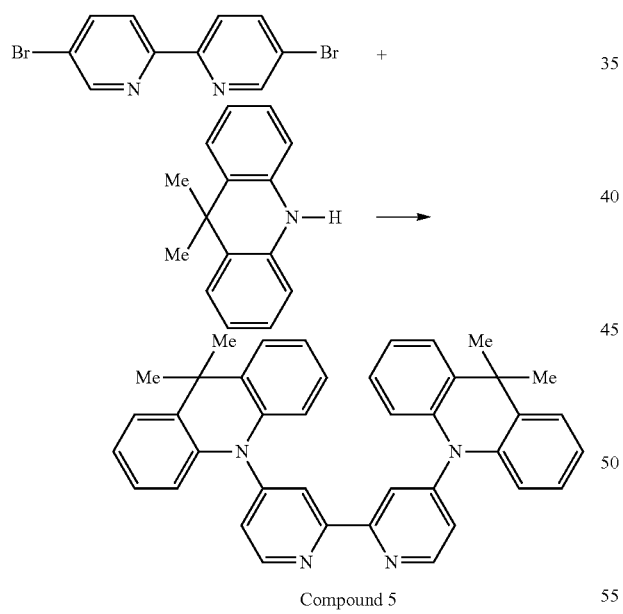

Compound 5

The synthesis process and the purification by column chromatography were performed in the same manner as in Synthesis Example 1 except that 5,5'-dibromobipyridine (3.14 g, 10 mmol) and dimethylacridan (5.02 g, 24 mmol) were used instead of 4,4'-dibromobipyridine (3.14 g, 10 mmol) and phenoxazine (4.40 g, 24 mmol), and thus the compound 5 was obtained at a yield amount of 1.71 g and a yield of 30%. Thereafter, the purified product of the compound 5 was subjected to sublimation purification under condition of 320° C. and 1 Pa or less.

$^1$H NMR (600 MHz, CDCl$_3$) δ 8.6-8.1 (2H), 8.0-7.6 (2H), 7.4-6.5 (18H), 1.5-1.9 (12H); MS (70 eV, EI) m/z=570 (M+), 555 (M$^+$-15)

Synthesis Example 6

Synthesis of Compound 6

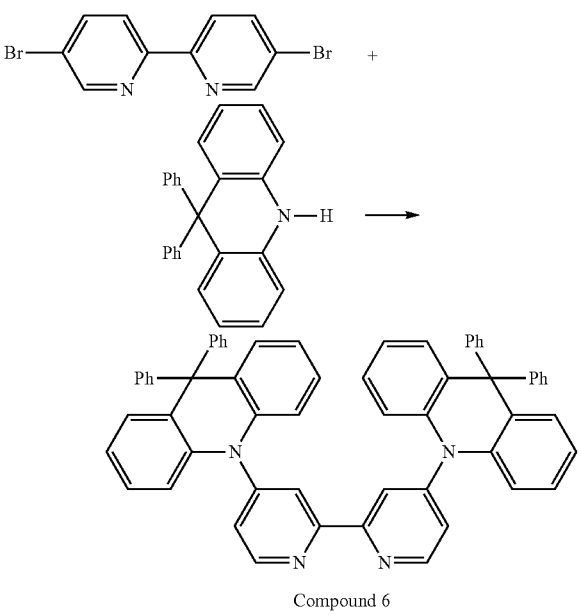

Compound 6

The synthesis process and the purification by column chromatography were performed in the same manner as in Synthesis Example 1 except that 5,5'-dibromobipyridine (1.57 g, 5 mmol) and diphenylacridan (4.00 g, 12 mmol) were used instead of 4,4'-dibromobipyridine (3.14 g, 10 mmol) and phenoxazine (4.40 g, 24 mmol), and thus the compound 6 was obtained at a yield amount of 1.97 g and a yield of 48%. Thereafter, the purified product of the compound 6 was subjected to sublimation purification under condition of 320° C. and 1 Pa or less.

$^1$H NMR (600 MHz, CDCl$_3$) δ 8.6-8.1 (2H), 8.0-7.5 (2H). 7.4-6.5 (38H); MS (70 eV, EI) m/z=819 (M+)

Comparative Synthesis Example 1

Synthesis of Comparative Compound 1

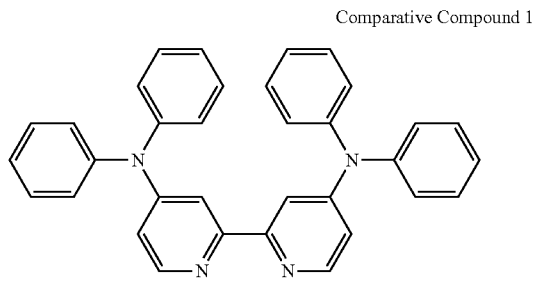 [SMILES: c1ccc(N(c2ccccc2)c2ccnc(-c3cc(N(c4ccccc4)c4ccccc4)ccn3)c2)cc1]

Comparative Compound 1

The synthesis process and the purification by column chromatography were performed in the same manner as in Synthesis Example 1 except that 5,5'-dibromobipyridine (3.14 g, 10 mmol) and diphenylamine (4.06 g, 24 mmol) were used instead of 4,4'-dibromobipyridine (3.14 g, 10 mmol) and phenoxazine (4.40 g, 24 mmol), and thus the comparative compound 1 was obtained at a yield amount of 4.91 g and a yield of 80%. Thereafter, the purified product of the comparative compound 1 was subjected to sublimation purification under condition of 320° C. and 1 Pa or less.

$^1$H NMR (600 MHz, CDCl$_3$) δ 8.5-8.1 (2H), 8.0-7.6 (2H), 7.4-6.5 (22H); MS (70 eV, EI) m/z=490 (M+)

Example 1

Preparation and Evaluation of Toluene Solution of Compound 1

A toluene solution of the compound 1 (concentration: 10$^{-5}$ mol/L) was prepared in a glove box under an Ar atmosphere.

Figure 2:
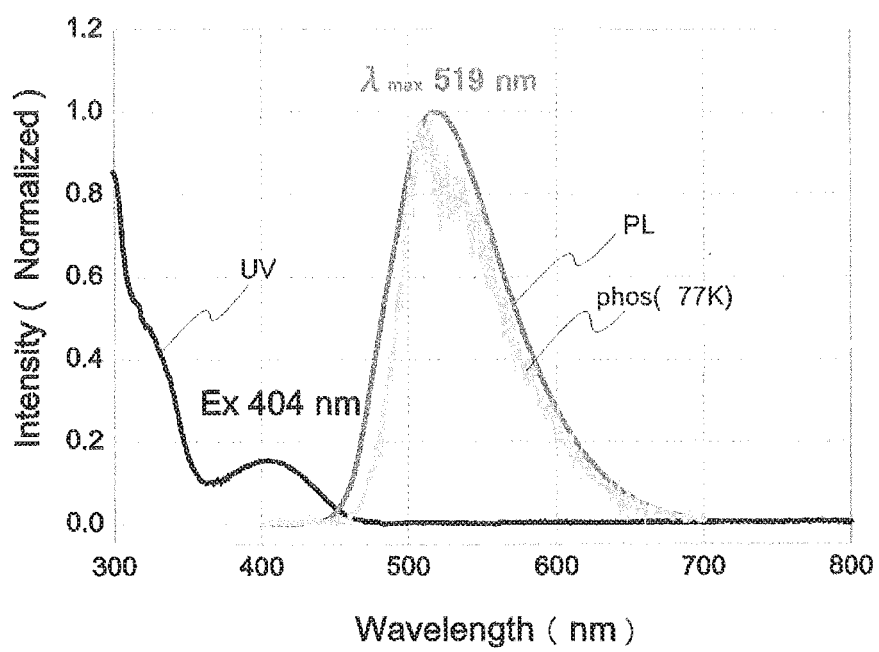
FIG. 2 shows the light emission spectra of the toluene solution of the compound 1 in Example 1.

The toluene solution of the compound 1 was measured for the photoluminescence spectrum with excitation light of 337 nm, and measured for the photoluminescence quantum efficiency in the air and after nitrogen substitution by nitrogen bubbling. The light emission spectra measured were the fluorescent spectrum (PL) and the phosphorescent spectrum (phos). The spectra are shown in FIG. 2. The photoluminescence quantum efficiency was 18% in the air and 88% after nitrogen substitution.

Figure 3:
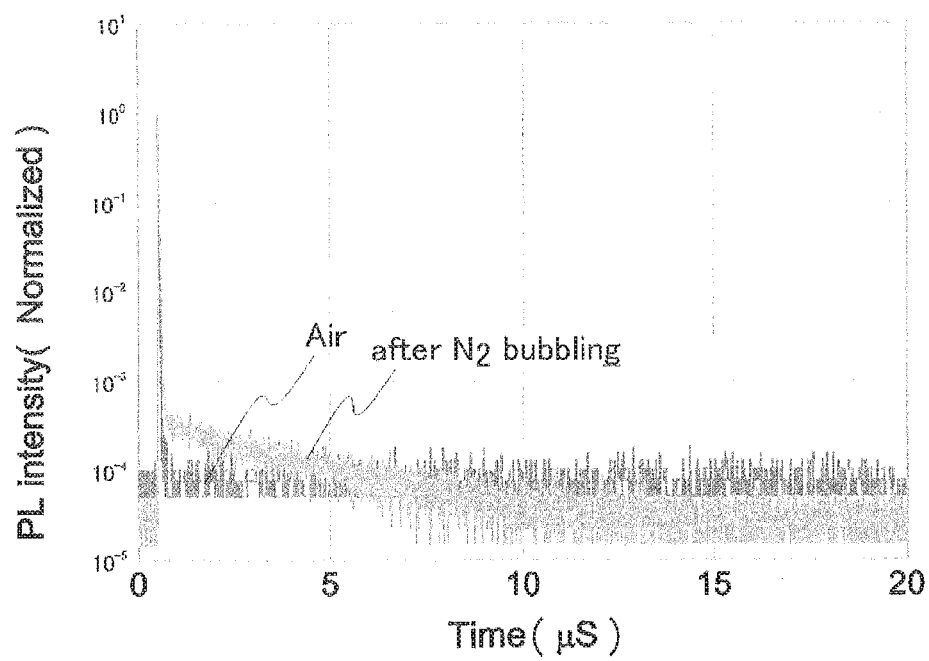
FIG. 3 shows the transient decay curves of the toluene solution of the compound 1 in Example 1.

The toluene solution of the compound 1 was measured for the transient decay curves in the air and after nitrogen substitution. The transient decay curves measured are shown in FIG. 3. The transient decay curves show the measurement result of the light emission lifetime in the process of deactivating the light emission intensity starting from the irradiation of the compound with excitation light. In the ordinary one-component light emission (fluorescent light or phosphorescent light), the light emission intensity decays monoexponentially. This means the linear decay in the case where the ordinate of the graph is in a semilogarithmic scale. In the transient decay curve of the compound 1 shown in FIG. 3, the linear component (fluorescent light) is observed in the initial stage of observation, but a component that deviates from the linearity appears after several microseconds. This is the light emission of the delayed component, and the signal obtained by adding the initial component forms a gentle curve having a long tail on the long time side. Thus, the measurement of the light emission lifetime confirmed that the compound 1 was a light-emitting material that exhibited a delayed component in addition to a fluorescent component. The light emission lifetime $\tau_1$ of the prompt fluorescence was 0.00636 ns in the air and 0.0192 μs after nitrogen substitution. The light emission lifetime $\tau_2$ of the delayed fluorescence was 2.54 μs after nitrogen substitution.

Example 2

Preparation and Evaluation of Thin Film Organic Photoluminescent Device of Compound 4

The compound 4 and mCP were vapor-deposited from separate vapor deposition sources on a quartz substrate by the vacuum vapor deposition method under a condition of a vacuum degree of 10$^{-4}$ Pa or less, so as to form a thin film having a thickness of 100 nm and a concentration of the compound 4 of 6.0% by weight, which was designated as a thin film organic photoluminescent device.

Figure 4:
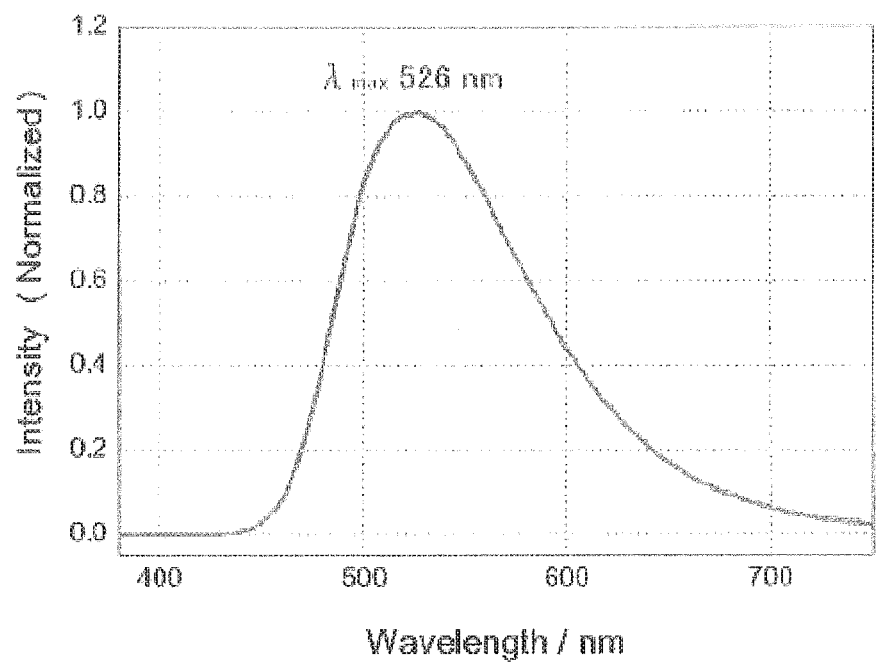
FIG. 4 shows the photoluminescence spectrum of the thin film organic photoluminescent device of the compound 4 in Example 2.
Figure 5:
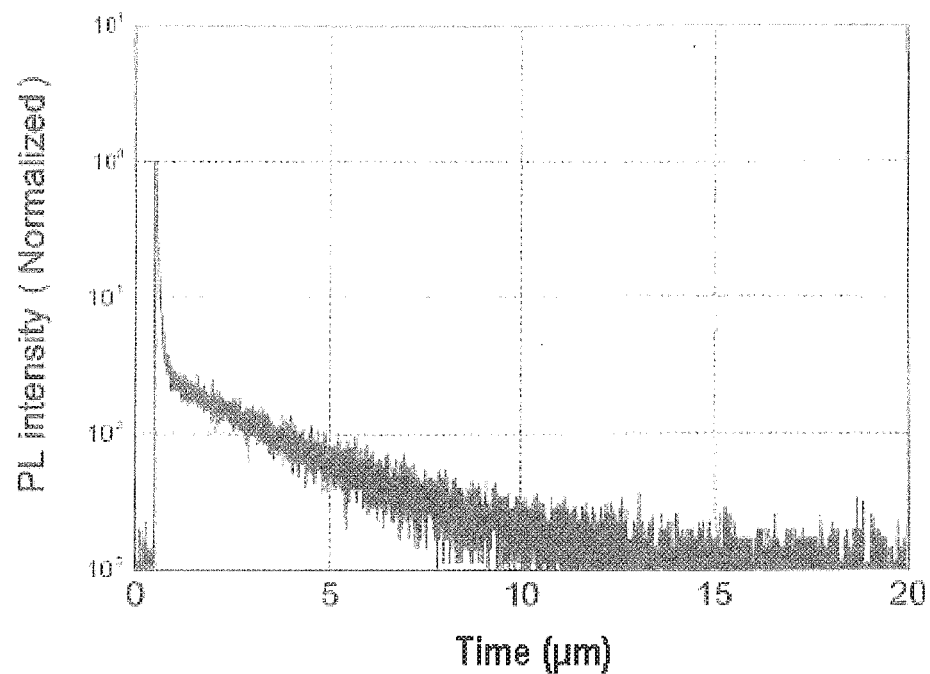
FIG. 5 shows the transient decay curve of the thin film organic photoluminescent device of the compound 4 in Example 2.

The organic photoluminescent device of the compound 4 was measured for the fluorescent spectrum and the transient decay curve with excitation light of 337 nm. The fluorescent spectrum measured is shown in FIG. 4, and the transient decay curve measured is shown in FIG. 5. The photoluminescence quantum efficiency was 47% in the air and 50% after nitrogen substitution. The light emission lifetime of the thin film organic photoluminescent device of the compound 4 was 59.6 ns for the prompt fluorescence $\tau_1$ and 2.88 μs for the delayed fluorescence $\tau_2$.

Comparative Example 1

Preparation and Evaluation of Thin Film Organic Photoluminescent Device of Comparative Compound 1

A thin film organic photoluminescent device was produced in the same manner as in Example 2 except that the comparative compound 1 was used instead of the compound 4.

Figure 6:
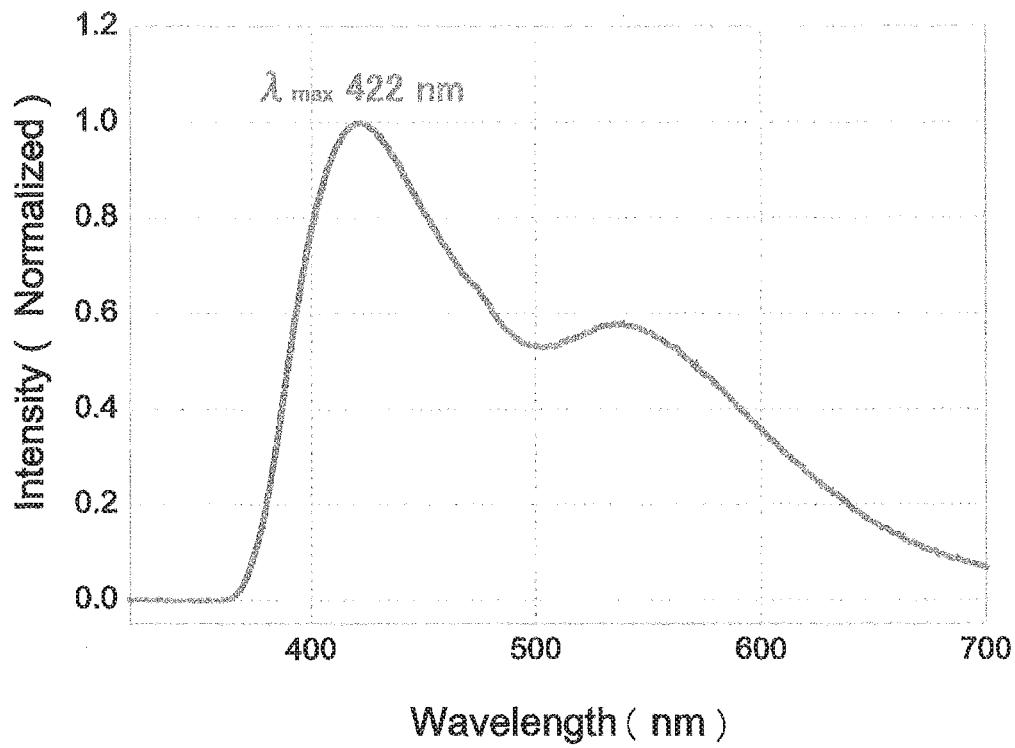
FIG. 6 shows the photoluminescence spectrum of the thin film organic photoluminescent device of the comparative compound 1 in Comparative Example 1.
Figure 7:
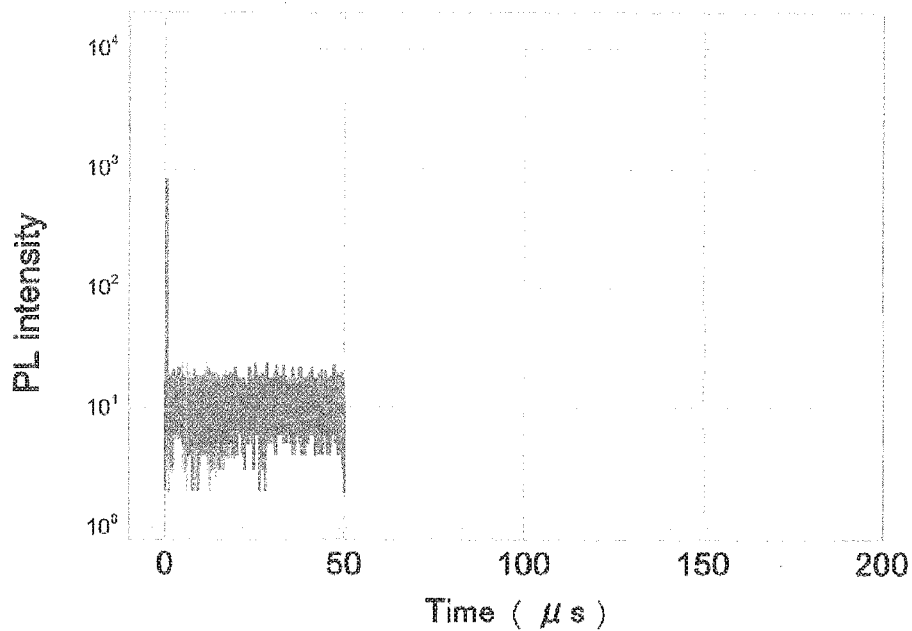
FIG. 7 shows the transient decay curve of the thin film organic photoluminescent device of the comparative compound 1 in Comparative Example 1.

The organic photoluminescent device of the comparative compound 1 was measured for the fluorescent spectrum and the transient decay curve with excitation light of 337 nm. The fluorescent spectrum measured is shown in FIG. 6, and the transient decay curve measured is shown in FIG. 7. In the fluorescent spectrum, a peak was observed at 550 nm in addition to 422 nm. The photoluminescence quantum efficiency was 18% in the air and 19% after nitrogen substitution. The light emission lifetime of the thin film organic photoluminescent device of the comparative compound 1 was 3.06 ns for the prompt fluorescence $\tau_1$, and no delayed fluorescence was observed.

Example 3

Preparation and Evaluation of Organic Electroluminescent Device of Compound 1

Thin films were laminated on a glass substrate having formed thereon an anode formed of indium tin oxide (ITO) having a thickness of 100 nm, by a vacuum vapor deposition method at a vacuum degree of 10$^{-3}$ Pa. Firstly, HAT-CN was formed to a thickness of 10 nm on ITO, and then Tris-PCz was formed to a thickness of 30 nm thereon. Subsequently, the compound 1 and mCBP were vapor-co-deposited thereon from separate vapor deposition sources to form a layer having a thickness of 30 nm, which was designated as a light-emitting layer. At this time, the concentration of the compound 1 was 6.0% by weight. T2T was then formed to a thickness of 10 nm, Bpy-TP2 was formed to a thickness of 40 nm, further lithium fluoride (LiF) was vacuum vapor-deposited to a thickness of 0.8 nm, and then aluminum (Al) was vapor-deposited to a thickness of 100 nm to form a cathode, thereby completing an organic electroluminescent device.

Figure 8:
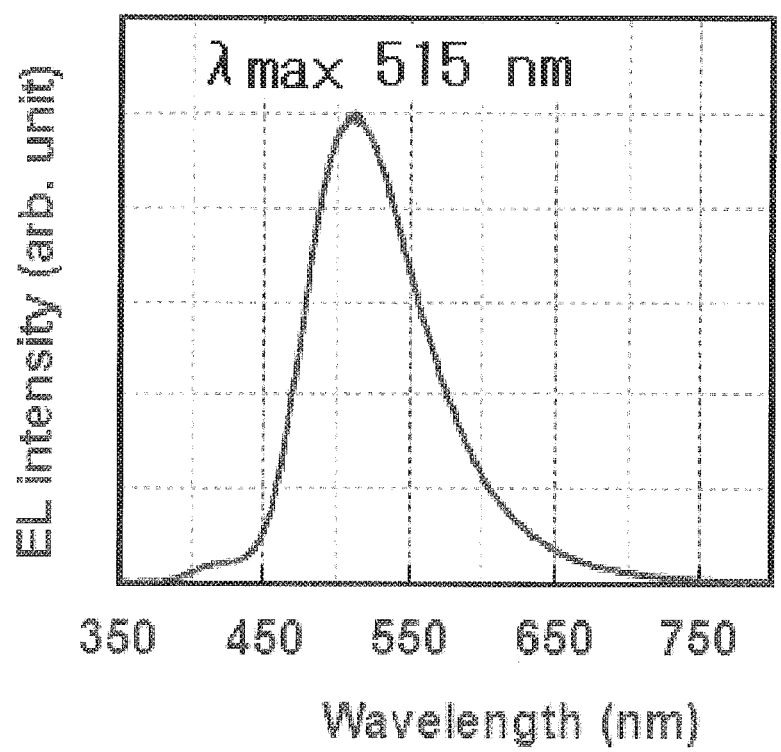
FIG. 8 shows the photoluminescence spectrum of the organic electroluminescent device of the compound 1 in Example 3.
Figure 9:
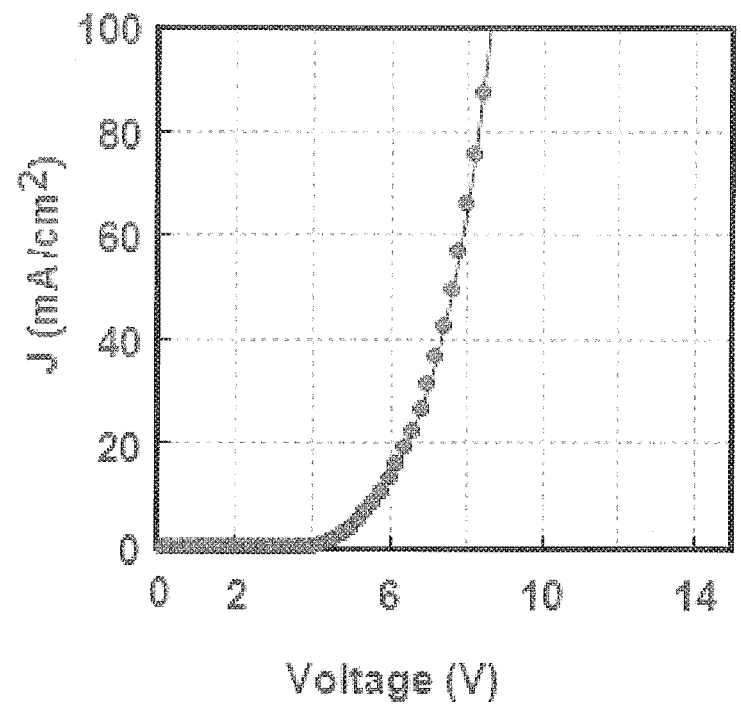
FIG. 9 is a graph showing the voltage-electric current density characteristics of the organic electroluminescent device of the compound 1 in Example 3.
Figure 10:
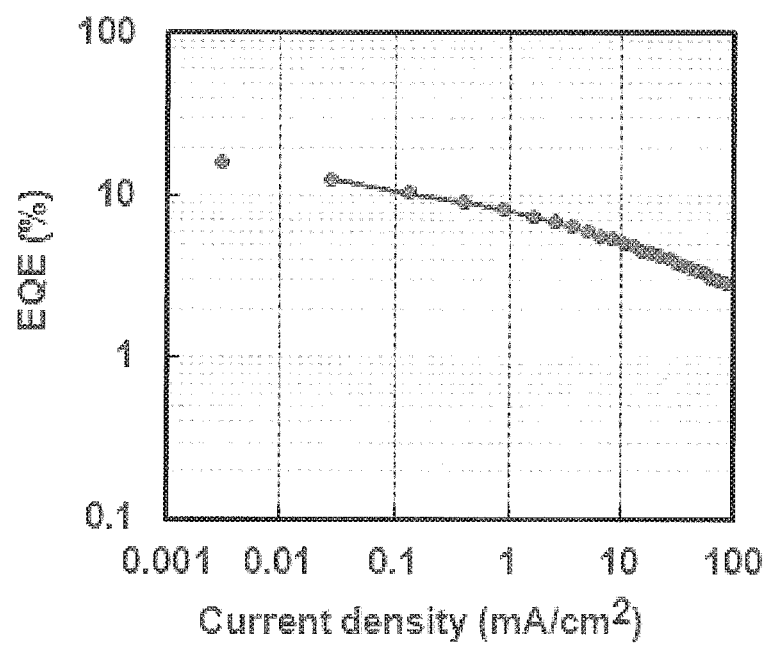
FIG. 10 is a graph showing the electric current density-external quantum efficiency characteristics of the organic electroluminescent device of the compound 1 in Example 3.

The photoluminescence spectrum of the organic electroluminescent device thus produced is shown in FIG. 8, the voltage-electric current density characteristics thereof are shown in FIG. 9, and the electric current density-external quantum efficiency characteristics thereof are shown in FIG. 10. The organic electroluminescent device using the compound 1 as a light-emitting material achieved a high external quantum efficiency of 12.7%. If an ideally balanced organic electroluminescent device is produced by using a fluorescent material having a light emission quantum efficiency of 100%, the external quantum efficiency of the fluorescent light emission may be from 5 to 7.5% assuming that the light extraction efficiency is from 20 to 30%. It has been ordinarily considered that this value is the theoretical limit value of an external quantum efficiency of an organic electroluminescent device using a fluorescent material. The organic electroluminescent device of the invention using the compound 1 is considerably excellent in such a point that a high external quantum efficiency that exceeds the theoretical limit value is achieved.

The compounds used in Examples all were delayed fluorescent materials emitting delayed fluorescent light. The compounds represented by the general formula (1) all have a high light emission quantum efficiency and exhibit excellent characteristics as a light-emitting material. On the other hand, the comparative compound 1 exhibited a lower light emission quantum efficiency than the compounds of Examples, and no delayed fluorescence was observed. It is presumed that this occurs since no ring is formed due to the absence of the bridge structure between the benzene rings in the amino group as the donor portion.

mCBP

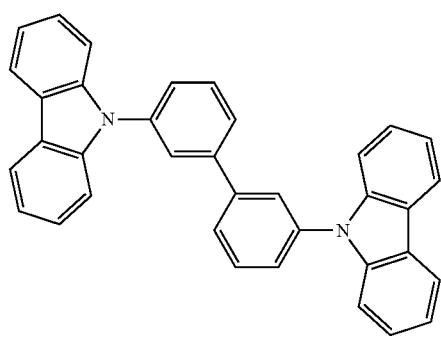

mCP

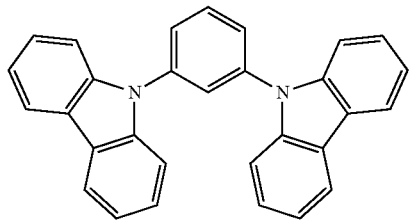

HATCN

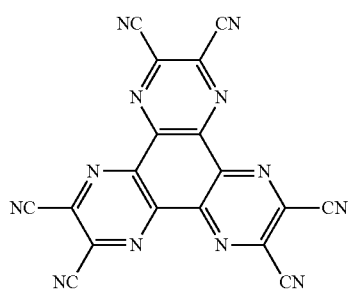

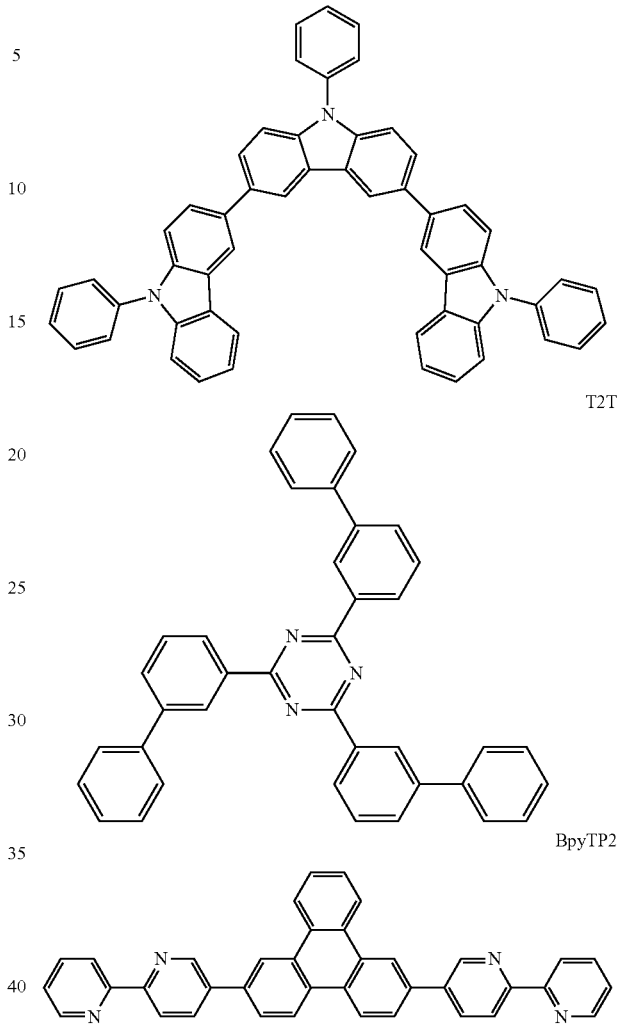

INDUSTRIAL APPLICABILITY

The compound of the invention is useful as a light-emitting material. Accordingly, the compound of the invention may be effectively used as a light-emitting material of an organic light-emitting device, such as an organic electroluminescent device. The compound of the invention includes a compound that emits delayed fluorescent light, and thus may be capable of providing an organic light-emitting device having a high light emission efficiency. Thus, the invention has high industrial applicability.

REFERENCE SIGNS LIST

1 substrate
2 anode
3 hole injection layer
4 hole transporting layer
5 light-emitting layer
6 electron transporting layer
7 cathode

What is claimed is:

1. A method for using a compound represented by the following Formula (1) as a light-emitting material:

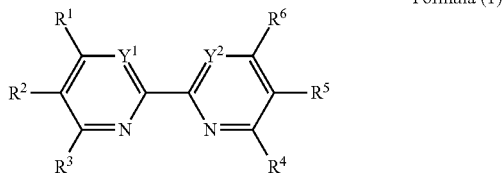

Formula (1)

wherein in the Formula (1), $Y^1$ and $Y^2$ each independently represent N or $C(R^7)$; and $R^1$ to $R^7$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsufonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms or a nitro group, provided that at least one of $R^1$ and $R^2$, and at least one of $R^5$ and $R^6$ each independently represent a group represented by the following Formula (2):

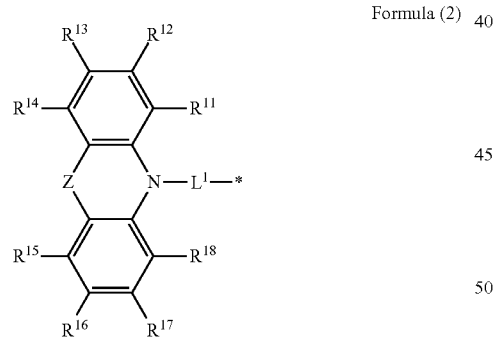

Formula (2)

wherein in the Formula (2), Z represents $C(R^{3a})(R^{3b})$, C=O, $N(R^{4a})$, O or S; $L^1$ represents a single bond or a substituted or unsubstituted arylene group; * represents a position bonded to the heterocyclic ring in the Formula (1); and $R^{11}$ to $R^{18}$, $R^{3a}$, $R^{3b}$ and $R^{4a}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkenyl group having from 5 to 20 carbon atoms or a nitro group, provided that $R^{11}$ and $R^{12}$, $R^{12}$ and $R^{13}$, $R^{13}$ and $R^{14}$, $R^{15}$ and $R^{16}$, $R^{16}$ and $R^{17}$, $R^{17}$ and $R^{18}$, and $R^{3a}$ and $R^{3b}$ each may be bonded to each other to form a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring or a cycloheptene ring.

2. The method according to claim 1, wherein the group represented by the Formula (2) is a group represented by any one of the following Formulae (3) to (7):

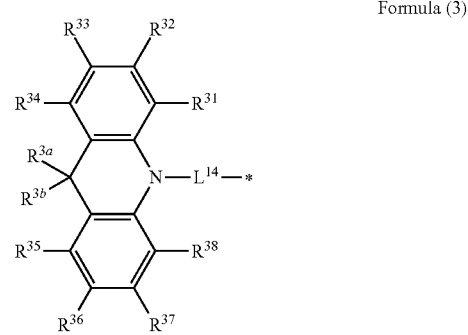

Formula (3)

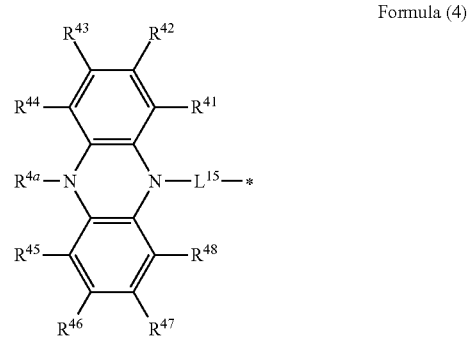

Formula (4)

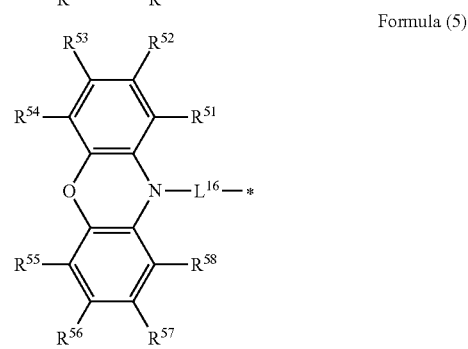

Formula (5)

Formula (6)

[structure with R61–R68, S, N—L17—*]

Formula (7)

[structure with R71–R78, O, N—L18—*]

wherein in the Formulae (3) to (7), $L^{14}$ to $L^{18}$ each represent a single bond or a substituted or unsubstituted arylene group; * represents a position bonded to the heterocyclic ring in the Formula (1); and $R^{31}$ to $R^{38}$, $R^{3a}$, $R^{3b}$, $R^{41}$ to $R^{48}$, $R^{4a}$, $R^{51}$ to $R^{58}$, $R^{61}$ to $R^{68}$, and $R^{71}$ to $R^{78}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms or a nitro group, provided that $R^{31}$ and $R^{32}$, $R^{32}$ and $R^{33}$, $R^{33}$ and $R^{34}$, $R^{35}$ and $R^{36}$, $R^{36}$ and $R^{37}$, $R^{37}$ and $R^{38}$, $R^{3a}$ and $R^{3b}$, $R^{41}$ and $R^{42}$, $R^{42}$ and $R^{43}$, $R^{43}$ and $R^{44}$, $R^{45}$ and $R^{46}$, $R^{46}$ and $R^{47}$, $R^{47}$ and $R^{48}$, $R^{51}$ and $R^{52}$, $R^{52}$ and $R^{53}$, $R^{53}$ and $R^{54}$, $R^{55}$ and $R^{56}$, $R^{56}$ and $R^{57}$, $R^{57}$ and $R^{58}$, $R^{61}$ and $R^{62}$, $R^{62}$ and $R^{63}$, $R^{63}$ and $R^{64}$, $R^{65}$ and $R^{66}$, $R^{66}$ and $R^{67}$, $R^{67}$ and $R^{68}$, $R^{71}$ and $R^{72}$, $R^{72}$ and $R^{73}$, $R^{73}$ and $R^{74}$, $R^{75}$ and $R^{76}$, $R^{76}$ and $R^{77}$, and $R^{77}$ and $R^{78}$ each may be bonded to each other to form a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring or a cycloheptene ring.

3. The method according to claim 1, wherein in the Formula (1), $R^2$ and $R^5$ each independently represent a group represented by the Formula (2).

4. The method according to claim 1, wherein in the Formula (1), $Y^1$ and $Y^2$ both represent N or both represent $C(R^7)$.

5. The method according to claim 1, wherein in the Formula (2), $L^1$ represents a single bond.

6. The method according to claim 1, wherein all the groups represented by the Formula (2) present in a molecule of the compound are the same as each other.

7. The method according to claim 1, wherein a molecule of the compound has a rotationally symmetric structure.

8. The method according to claim 1, wherein a molecule of the compound has an axisymmetric structure.

9. A method for using a compound represented by the following Formula (1) as a delayed fluorescent emitter:

Formula (1)

[structure with $R^1$, $R^2$, $R^3$, $Y^1$, $Y^2$, $R^4$, $R^5$, $R^6$, N, N]

wherein in the Formula (1), $Y^1$ and $Y^2$ each independently represent N or $C(R^7)$; and $R^1$ to $R^7$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms or a nitro group, provided that at least one of $R^1$ and $R^2$, and at least one of $R^5$ and $R^6$ each independently represent a group represented by the following Formula (2):

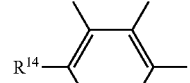

Formula (2)

wherein in the Formula (2), Z represents C(R$^{3a}$)(R$^{3b}$), C=O, N(R$^{4a}$), O or S; L$^1$ represents a single bond or a substituted or unsubstituted arylene group; * represents a position bonded to the heterocyclic ring in the Formula (1); and R$^{11}$ to R$^{18}$, R$^{3a}$, R$^{3b}$ and R$^{4a}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkenyl group having from 5 to 20 carbon atoms or a nitro group, provided that R$^{11}$ and R$^{12}$, R$^{12}$ and R$^{13}$, R$^{13}$ and R$_{14}$, R$^{15}$ and R$^{16}$, R$^{16}$ and R$^{17}$, R$^{17}$ and R$^{18}$, and R$^{3a}$ and R$^{3b}$ each may be bonded to each other to form a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring or a cycloheptene ring.

10. An organic light-emitting device containing a compound represented by the following Formula (1):

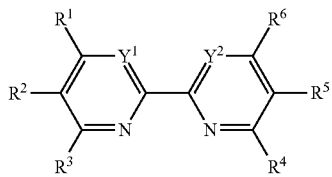

Formula (1)

wherein in the Formula (1), Y$^1$ and Y$^2$ each independently represent N or C(R$^7$); and R$^1$ to R$^7$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms or a nitro group, provided that at least one of R$^1$ and R$^2$, and at least one of R$^5$ and R$^6$ each independently represent a group represented by the following Formula (2):

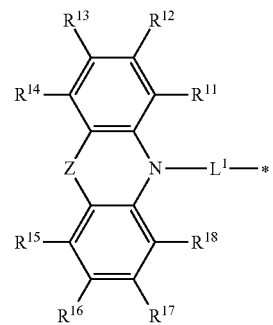

Formula (2)

wherein in the Formula (2), Z represents C(R$^{3a}$)(R$^{3b}$), C=O, N(R$^{4a}$), O or S; L$^1$ represents a single bond or a substituted or unsubstituted arylene group; * represents a position bonded to the heterocyclic ring in the Formula (1); and R$^{11}$ to R$^{18}$, R$^{3a}$, R$^{3b}$ and R$^{4a}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkenyl group having from 5 to 20 carbon atoms or a nitro group, provided that R$^{11}$ and R$^{12}$, R$^{12}$ and R$^{13}$, R$^{13}$ and R$^{14}$, R$^{15}$ and R$^{16}$, R$^{16}$ and R$^{17}$, R$^{17}$ and R$^{18}$, and R$^{3a}$ and R$^{3b}$ each may be bonded to each other to form a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring or a cycloheptene ring.

11. The organic light-emitting device according to claim 10, wherein the organic light-emitting device emits delayed fluorescent light.

12. The organic light-emitting device according to claim 10, wherein the organic light-emitting device is an organic electroluminescent device.

13. A compound represented by the following Formula (1'):

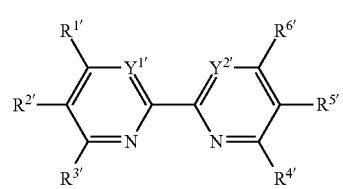

Formula (1')

wherein in the Formula (1'), Y$^{1'}$ and Y$^{2'}$ each independently represent N or C(R$^{7'}$); and R$^{1'}$ to R$^{7'}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms or a nitro group, provided that at least one of $R^{1'}$ and $R^{2'}$, and at least one of $R^{5'}$ and $R^{6'}$ each independently represent a group represented by the following Formula (2'):

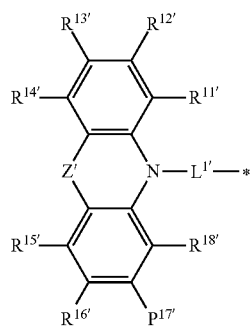

Formula (2')

wherein in the Formula (2'), Z' represents $C(R^{3a'})(R^{3b'})$, C=O, $N(R^{4a'})$, O or S; $L^{1'}$ represents a single bond or a substituted or unsubstituted arylene group; * represents a position bonded to the heterocyclic ring in the Formula (1'); and $R^{11'}$ to $R^{18'}$, $R^{3a'}$, $R^{3b'}$ and $R^{4a'}$ each independently represent a hydrogen atom, a hydroxyl group, a halogen atom, a cyano group, an alkyl group having from 1 to 20 carbon atoms, an alkoxy group having from 1 to 20 carbon atoms, an alkylthio group having from 1 to 20 carbon atoms, an alkyl-substituted amino group having from 1 to 20 carbon atoms, an acyl group having from 2 to 20 carbon atoms, an aryl group having from 6 to 40 carbon atoms, a heteroaryl group having from 3 to 40 carbon atoms, an alkenyl group having from 2 to 10 carbon atoms, an alkynyl group having from 2 to 10 carbon atoms, an alkoxycarbonyl group having from 2 to 10 carbon atoms, an alkylsulfonyl group having from 1 to 10 carbon atoms, a haloalkyl group having from 1 to 10 carbon atoms, an amide group, an alkylamide group having from 2 to 10 carbon atoms, a trialkylsilyl group having from 3 to 20 carbon atoms, a trialkylsilylalkyl group having from 4 to 20 carbon atoms, a trialkylsilylalkenyl group having from 5 to 20 carbon atoms, a trialkylsilylalkynyl group having from 5 to 20 carbon atoms or a nitro group, provided that $R^{11'}$ and $R^{12'}$, $R^{12'}$ and $R^{13'}$, $R^{13'}$ and $R^{14'}$, $R^{15'}$ and $R^{16'}$, $R^{16'}$ and $R^{17'}$, $R^{17'}$ and $R^{18'}$, and $R^{3a'}$ and $R^{3b'}$ each may be bonded to each other to form a benzene ring, a naphthalene ring, a pyridine ring, a pyridazine ring, a pyrimidine ring, a pyrazine ring, a pyrrole ring, an imidazole ring, a pyrazole ring, a triazole ring, an imidazoline ring, an oxazole ring, an isoxazole ring, a thiazole ring, an isothiazole ring, a cyclohexadiene ring, a cyclohexene ring, a cyclopentene ring, a cycloheptatriene ring, a cycloheptadiene ring or a cycloheptene ring.

* * * * *